United States Patent [19]

Johe

[11] Patent Number: 5,753,506
[45] Date of Patent: May 19, 1998

[54] ISOLATION PROPAGATION AND DIRECTED DIFFERENTIATION OF STEM CELLS FROM EMBRYONIC AND ADULT CENTRAL NERVOUS SYSTEM OF MAMMALS

[75] Inventor: Karl K. Johe, Potomac, Md.

[73] Assignee: CNS Stem Cell Technology, Inc., Bethesda, Md.

[21] Appl. No.: 719,450

[22] Filed: Sep. 25, 1996

Related U.S. Application Data

[60] Provisional application No. 60/018,206, May 23, 1996.

[51] Int. Cl.$^6$ .................................................. C12N 5/08
[52] U.S. Cl. ...................... 435/377; 435/325; 435/366; 435/368
[58] Field of Search .................. 435/240.2, 240.21, 435/240.23, 240.1, 325, 347, 352, 363, 366, 368, 375, 377

[56] References Cited

U.S. PATENT DOCUMENTS 5,589,376  12/1996  Audeeson et al. .................... 435/240.2

FOREIGN PATENT DOCUMENTS

| WO 94/02593 | 2/1994 | WIPO . |
| WO 94/10292 | 5/1994 | WIPO . |
| WO 96/09543 | 3/1996 | WIPO . |

OTHER PUBLICATIONS

Von Visger, Experimental Neurology 128: 34–40, 1994.
Vicario–Abejon, Neuron 15: 105–114, 1995.
McKay, R., Johe, K., et al., Stem cells in the developing and adult brain, Cellular and Molecular Treatments of Neurologic Diseases, Abstract, Sep. 7–10, 1995, Cambridge, Massachusetts.
Davis, A.A. & Temple, S., Nature 372, 263–266 (1994).
Reynolds, B., Tetzlaff, W. & Weiss, S., J. Neurosci. 12, 4565–4574 (1992).
Ray, J. Peterson, D., Schinstine, M. & Gage, F. Proc. Natl. Acad. Sci. USA 90,3602–3606 (1993); Genetics 9,265–260 (1995).
Vicario–Abejon, C., Johe, K., Hazel, T., Collazo, D. & McKay, R., Neuron 15, 105–114 (1995).
Sabate, O., Horellou, P., Vigne, E., Colin, P., Perricaudet, M., Buc–Caron, M.-H. & Mallet, J., Nature Genetics 9, 256–260 (1995).
Svendsen, C.N. & Rosser, A.E., Trends in Neuroscience 18, 465–466 (1995).
Gage, F.H., Ray, J. & Fisher, L.J. Annu. Rev. Neurosci. 18, 159–192 (1995).
Gage, F.H., Coates, P.W., Palmer, T.D., Kuhn, H.G., Fisher, L.J., Suhonen, J.O., Peterson, D.A., Suhr S.T. & Ray, J., Proc. Natl. Acad. Sci. USA 92, 11879–11883 (1995).
Svendsen, C.N., Fawcett, J.W., Bentlage, C. & Dunnett, S.B., Exp. Brain Res. 102, 407–44114 (1995).
Hermanson, M., Olsson, T., Wetermark, B. & Funa K., Exp. Brain Res. 102, 415–422 (1995).
Kilpatrick, T.J., Richards, L.J., and Bartlett, P.F., Mol. Cell. Neurosci. 6, 2–15 (1995).
Ray, J. and Gage, F.H., J. Neurosci. 14, 3548–3564 (1994).
Gritti, A., et al., J. Neurosci. 16, 1091–1100 (1996).
Vescovi, A.L., Reynolds, B.A., Fraser, D.D., and Weiss, S., Neuron 11, 951–966 (1993).
Ahmed, S., Reynolds, B.A., and Weiss, S., J. Neurosci. 15, 5765–5778 (1995).
Kilpatrick, T.J., and Bartlett, P.F., J. Neurosci. 15, 3653–3661 (1995).
Baetge, E.E., Ann. N.Y. Acad. Sci. 695, 285 (1993).
Bartlett, P.F. et al., Clin. Exp. Pharm. Physiol. 22, 559–562 (1995).
Lois et al (1993) Proc. Nat'l Acad. Sci. 90: 2074–2077.

*Primary Examiner*—Marianne P. Allen
*Attorney, Agent, or Firm*—Bell, Boyd & Lloyd

[57] ABSTRACT

The present invention reveals an in vitro procedure by which a homogeneous population of multipotential precursor cells from mammalian embryonic neuroepithelium (CNS stem cells) can be expanded up to $10^9$ fold in culture while maintaining their multipotential capacity to differentiate into neurons, oligodendrocytes, and astrocytes. Chemically defined conditions are presented that enable a large number of neurons, up to 50% of the expanded cells, to be derived from the stem cells. In addition, four factors—PDGF, CNTF, LIF, and T3—have been identified which, individually, generate significantly higher proportions of neurons, astrocytes, or oligodendrocytes. These defined procedures permit a large-scale preparation of the mammalian CNS stem cells, neurons, astrocytes, and oligodendrocytes under chemically defined conditions with efficiency and control. These cells should be an important tool for many cell- and gene-based therapies for neurological disorders.

16 Claims, 11 Drawing Sheets

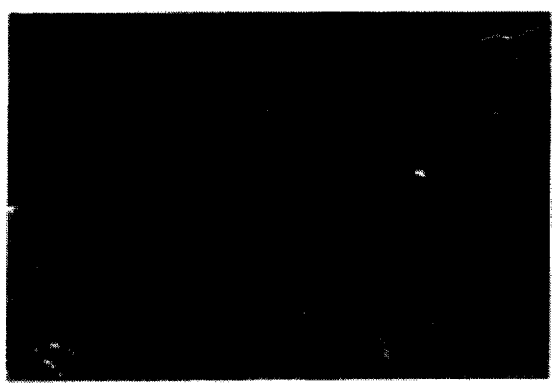
FIG. 5A                                FIG. 5B
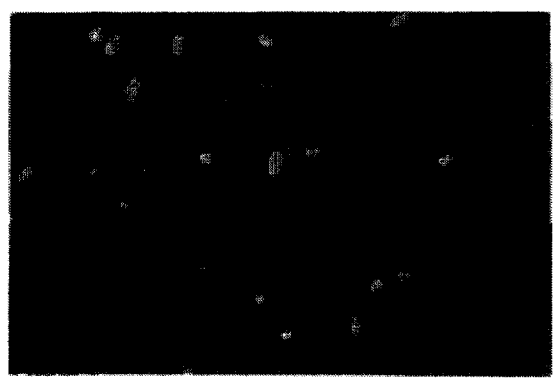
FIG. 5C                                FIG. 5D
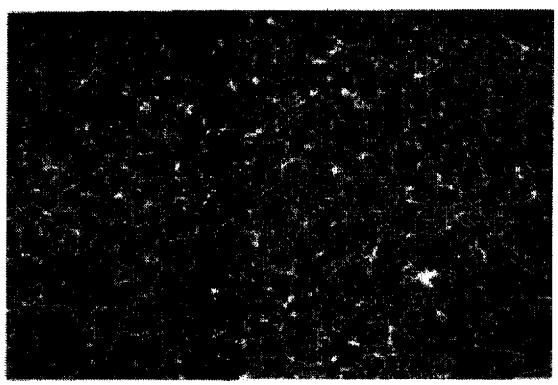
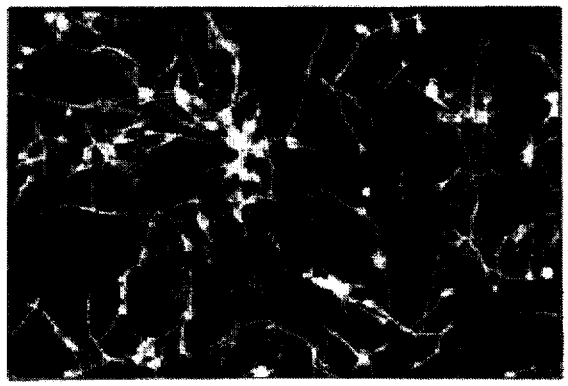
FIG. 5E                                FIG. 5F

| | | | |
|---|---|---|---|
| Undifferentiated CTX Stem Cells | 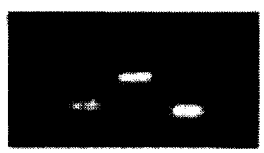 FIG. 8A |  FIG. 8B | 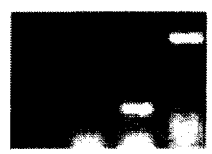 FIG. 8C |
| Differentiated Stem-derived Neurons |  FIG. 8D |  FIG. 8E |  FIG. 8F |
| Adult Whole Brain |  FIG. 8G |  FIG. 8H | 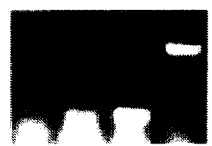 FIG. 8I |

ISOLATION PROPAGATION AND DIRECTED DIFFERENTIATION OF STEM CELLS FROM EMBRYONIC AND ADULT CENTRAL NERVOUS SYSTEM OF MAMMALS

BACKGROUND OF THE INVENTION

This application claims the benefit of U.S. Provisional application No. 60/018,206, filed May 23, 1996, now abandoned.

1. Field of the Invention

The present invention relates to a technology where stem cells from embryonic and adult brain are isolated, propagated, and differentiated efficiently in culture to generate large numbers of nerve cells. This technology, for the first time, enables one to generate large numbers of many different kinds of neurons found in a normal brain and provides a new foundation for gene therapy, cell therapy, novel growth factor screening, and drug screening for nervous system disorders.

2. Description of the Related Art

The brain is composed of highly diverse nerve cell types making specific interconnections and, once destroyed, the nerve cells (neurons) do not regenerate. In addition, the brain is protected by a blood-brain barrier that effectively blocks the flow of large molecules into the brain, rendering peripheral injection of potential growth factor drugs ineffective. Thus, a major challenge currently facing the biotechnology industry is to find an efficient mechanism for delivering potential gene therapy products directly into the brain in order to treat nervous system disorders.

Moreover, for a degenerative disease like Parkinson's, the most comprehensive approach to regain a lost neural function may be to replace the damaged cells with healthy cells, rather than just a single gene product. Thus, current and future success of gene therapy and cell therapy depends upon development of suitable cells that can (1) carry a healthy copy of a disease gene (i.e., a normal gene), (2) be transplanted into the brain, and (3) be integrated into the host's neural network. This development ideally requires cells of neuronal origin that (1) proliferate in culture to a large number, (2) are amenable to various methods of gene transfer, and (3) integrate and behave as the cells of a normal brain. However, there have been no such cells for therapeutic purposes since neurons do not divide and therefore cannot be propagated in culture.

As alternatives, various transformed cells of neural and non-neural origins such as glias, fibroblasts, and even muscle cells, which can be proliferated in culture, have been used as possible vehicles for delivering a gene of interest into brain cells. However, such cells do not and cannot be expected to provide neuronal functions. Another alternative approach has been to force a neural cell of unknown origin to divide in culture by genetically modifying some of its properties, while still retaining some of its ability to become and function as a neuron. Although some "immortalized" cells can display certain features of a neuron, it is unclear whether these altered cells are truly a viable alternative for clinical purposes.

A developing fetal brain contains all of the cells germinal to the cells of an adult brain as well as all of the programs necessary to orchestrate them toward the final network of neurons. At early stages of development, the nervous system is populated by germinal cells from which all other cells, mainly neurons, astrocytes, and oligodendrocytes, derive during subsequent stages of development. Clearly, such germinal cells that are precursors of the normal brain development would be ideal for all gene-based and cell-based therapies if these germinal cells could be isolated, propagated, and differentiated into mature cell types.

The usefulness of the isolated primary cells for both basic research and for therapeutic application depends upon the extent to which the isolated cells resemble those in the brain. Just how many different kinds of precursor cells there are in the developing brain is unknown. However, several distinct cell types may exist:

- a precursor to neuron only ("committed neuronal progenitor" or "neuroblast"),
- a precursor to oligodendrocyte only ("oligodendroblast"),
- a precursor to astrocyte only ("astroblast"),
- a bipotential precursor that can become either neuron or oligodendrocyte, neuron or astrocyte, and oligodendrocyte or astrocyte, and
- a multipotential precursor that maintains the capacity to differentiate into any one of the three cell types.

Fate mapping analysis and transplantation studies in vivo have shown that different neuronal types and non-neuronal cells can be derived from the same precursor cells[1-5]. In vitro analyses have also suggested that multipotential cells are present in the developing brain[6,7]. Lineage analysis alone, however, does not directly identify the multipotential cells; nor does it define the mechanisms that drive them to different fates. Precursor cells from the central nervous system (CNS) have been expanded in vitro and differentiation into neurons and glia has been observed[8-12] and, as detailed below, markedly different cell types have been obtained even when the culture conditions used were seemingly the same.

Because of the current lack of understanding of histogenesis during brain development, many investigators have used various terms loosely to describe the cells that they have studied, e.g., neuronal progenitor, neural precursor, neuroepithelial precursor, multipotential stem cell, etc. Thus, the nature of the cells so far described in the literature and culture conditions for obtaining them can only be compared to each other by their reported differentiation capacity. The entire subject of the isolation, characterization, and use of stem cells from the CNS has recently been reviewed[33,34,38].

In summary, conditions have not been found to date, despite many reports, to successfully identify, propagate, and differentiate multipotential stem cells. A useful compilation of studies reporting culture of CNS precursor cells is found in Table 3, p. 172, of a recent review[34] and further extended below.

Vicario-Abelon, C., Johe, K., Hazel, T., Collazo, D. & McKay, R., Functions of basic fibroblast growth factor and neurotrophins in the differentiation of hippocampal neurons, Neuron 15, 105–114 (1995)[12].

Cells expanded by Vicario-Abejon et al. are significantly different from those described in the present invention although the starting tissue (embryonic hippocampus), the mitogen (basic fibroblast growth factor, bFGF), and the basal medium (N2) are similar in both reports. Almost all of the cells expanded by Vicario-Abejon et al. failed to differentiate into any cell types but died in the absence of bFGF (as stated in the paper, pg. 106). This is also reflected in FIG. 3 of the paper where the number of MAP2 positive neurons is exceedingly low (50–100 cells out of an initial cell number of approximately 80,000 per well; i.e., far less than 1% in all reported conditions). Thus, differences in culture conditions, subtle as they may be, can yield cells with significantly different properties and this is, in fact, consistent with the main observation of the present invention that the extracellular environment can shift the developmental properties of the CNS stem cells.

Vicario-Abejon et al. used the following culture conditions which differ from the those described in the present invention:

1. Used enzymatic dissociation, 0.1–0.25% trypsin+0.4% DNAse I for the initial tissue dissociation as well as subsequent passaging. In the present invention, enzymatic dissociation effectively causes proteolyses of FGF receptors and causes cells to become unresponsive to bFGF and leads to differentiation.
2. Used 10% fetal bovine serum to stop the trypsin activity and to prime the cells from 4 hours to overnight before switching to serum free medium. In the present invention, serum even at less than 1% concentration shifts stem cells to astrocytic fate.
3. Cells were seeded at much higher density of 45,000 cells per $cm^2$ and then grown to confluence before passaging by trypsin and serum. In the present invention, high cell density inhibits proliferation and causes spontaneous differentiation even in the presence of bFGF.
4. bFGF was given only intermittently every 2–3 days, and at 5 ng/ml, less than the optimal concentration disclosed in the present invention. This condition leads to partial differentiation of cells and subsequent heterogeneity of cell types in culture.
5. Basal medium consisting of "N2" components consisted of 5 ng/ml insulin, less than the optimal concentration disclosed in the present invention.

Ray. J., Peterson. D., Schinstine. M. & Gage. F., Proliferation, differentiation, and long-term culture of primary hippocampal neurons, *Proc. Natl. Acad. Sci. U.S.A.* 90, 3602–3606 (1993)[10].

This study used culture conditions that are very similar to those described by Vicario-Abejon et al.—bFGF as the primary mitogen, serum-free medium, and E16 hippocampus. However, it reports isolation and expansion of a precursor population—neuroblasts—quite different from the cells of Vicario-Abejon et al. (undefined) as well as the multipotential stem cells described in the present invention. The reported cells had the following properties which markedly contrast from those of CNS stem cells:

1. The expanded cells under the reported condition are mitotic neurons with antigenic expressions of neurofilament, nestin, neuron-specific enolase, galactocerebroside, and MAP2 (Table I, p. 3604). The expanding CNS stem cells reported in the present invention express nestin, only, are negative for the above antigens, and are, therefore, a molecularly distinct population of cells from those described by Ray et al.
2. Ultrastructural analysis of the expanded cells in culture "demonstrated their histotypic neuronal morphology". The expanding CNS stem cells exhibit entirely different, non-neuronal morphology.
3. The mitotic "neurons" had a doubling time of 4 days and could be passaged and grown as continuous cell lines. The CNS stem cells double at every 20–24 hours and exhibit a characteristic regression of mitotic and differentiative capacity over time so that they cannot be maintained as stable cell lines indefinitely.
4. The culture system by Ray et al. generates "nearly pure neuronal cell cultures". The culture system in the present invention generates multipotential stem cells that can differentiate into all three major cell types of the brain, neurons, oligodendrocytes, and astrocytes.

Ray et al. used the following culture conditions which differ from those of the present invention.

1. Embryonic hippocampi were mechanically triturated without the use of an enzyme; however, cells were plated approximately 100,000 cells per $cm^2$, optimal for neuronal survival, but almost 10 times higher cell density than optimal for expansion of CNS stem cells.
2. bFGF was given at 20 ng/ml, intermittently, at every 3–4 days.
3. Basal "N2" medium contained 5 μg/ml insulin, less than optimal. Medium change was also prolonged at every 3–4 days.
4. Cells were passaged by using trypsin.

In conclusion, even seemingly small differences in culture conditions can result in isolation of vastly different cell types.

Ray, J. and Gage, F. H., Spinal cord neuroblasts proliferate in response to basic fibroblast growth factor, *J. Neurosci.* 14, 3548–3564 (1994)[39].

Ray and Gage report isolation and propagation of cells "that have already committed to a neuronal pathway are and expressing neuronal phenotypes (neuroblasts)" from spinal cord using bFGF. Again, although the primary mitogen is bFGF, their culture conditions are different and obtained cells markedly different from CNS stem cells.

1. E14–E16 spinal cord was used, a much later stage of development than optimal for stem cells.
2. The tissue was dissociated enzymatically by papain and DNase.
3. Initial plating was done in 10% fetal bovine serum.
4. There was a preliminary enrichment for a non-adherent cell population.
5. There was intermittent medium change and bFGF supplement, every 3–4 days.

Gage. F. H., Coates, P. W., Palmer. T. D., Kuhn. H. G., Fisher, L. J., Suhonen. J. O., Peterson, D. A., Suhr, S. T. & Ray, J., Survival and differentiation of adult neuronal progenitor cells transplanted to the adult brain. *Proc. Natl. Acad. Sci. USA* 92, 11879– 11883 (1995)[35].

Gage et al. report isolation, propagation, and transplantation of cells from adult hippocampus. These mixtures of cells were maintained in culture for one year through multiple passages. 80% of them exhibit rather unusual properties such as co-expressing glial and neuronal antigens while remaining mitotic. These properties are not exhibited by stem cells isolated from the adult strial subventricular zone.

Again, using bFGF as a primary mitogen, the authors derived markedly different cells than CNS stem cells reported in the present invention.

Gritti. A. et al., Multipotential stem cells from the adult mouse brain proliferate and self-renew in response to basic fibroblast growth factor. *J. Neurosci.* 16, 1091–1100 (1996)[40].

These authors report isolation and propagation of multipotential stem cells from the subventricular zone of adult brain by using bFGF. A significant difference in culture conditions used by Gritti et al. is that the cells are propagated as aggregated spheres without attachment to plate surface. Culture condition by Gritti et al. requires this aggregation of cells into spheres, using either bFGF or epidermal growth factor (EGF), as an essential step for propagating multipotential cells. This aggregation step alone essentially distinguishes the reported culture system from that of the present invention. The aggregation promotes undefined cell-cell interactions and results in uncontrollable differentiation/fate-shifts and overall in much less expansion and differentiation. Furthermore, this culture system and the result obtained by Gritti et al. are limited to adult brain where extremely small number of cells were obtained ($10^5$ cells per brain) and have not been extended to various regions of embryonic brain.

The procedure in the present invention permits propagation of stem cells throughout the developing CNS as well as the striatum of the adult brain. It also uses adherent culture and actively avoids cell-cell contact and high cell density. As a result, it permits much more efficient expansion of the cells in an undifferentiated multipotential state and much more precise and efficient control over differentiation of the expanded cells.

Reynolds, B. & Weiss, S., Generation of neurons and astrocytes from isolated cells of the adult mammalian central nervous system, *Science* 255, 1707–1710 (1992)[15].

Reynolds, B., Tetzlaff, W. & Weiss, S., A multipotent EGF-responsive striatal embryonic progenitor cell produces neurons and astrocytes, *J. Neurosci.* 12, 4565–4574 (1992)[9].

Vescovi, A. L., Reynolds, B. A., Fraser, D. D., and Weiss, S., bFGF regulates the proliferative fate of unipotent (neuronal) and bipotent (neuronal/astorglial) EGF-generated CNS progenitor cells, *Neuron* 11, 951–966 (1993)[41].

These three studies describe the original sphere cultures of neural precursor cells from adult and embryonic brain using EGF (epidermal growth factor). The expanded cells differentiate into neurons and astrocytes, but not into oligodendrocytes, and thus are thought to be a bipotential population, rather than multipotential. Another distinguishing property of the cells is that they respond only to EGF and not to bFGF, in particular whereas CNS stem cells respond similarly to both EGF and bFGF. Again, the sphere culture conditions are not comparable to those employed in the present invention because they require cell aggregation in which many additional undefined interactions are expected to occur.

Ahmed, S., Reynolds, B. A., and Weiss, S., BDNF enhances the differentiation but not the survival of CNS stem cell-derived neuronal precursors, *J. Neurosci.* 15, 5765–5778 (1995)[42].

This paper reports the effects of brain-derived growth factor (BDNF) on sphere cultures of embryonic neural precursor cells propagated with EGF. There is no further enhancement of the culture system per se.

Svendsen, C. N., Fawcett, J. W., Bentlage, C. & Dunnett, S. B., Increased survival of rat EGF-generated CNS precursor cells using B27 supplemented medium. *Exp. Brain Res.* 102, 407–414 (1995)[36].

This study utilizes the sphere culture with EGF as described above to test a commercially available medium supplement called "B27". The study simply reports that use of B27 enhances cell survival (not neuronal survival) in a mixed culture containing neurons, astrocytes, and oligodendrocytes.

Kilpatrick, T. J. and Bartlett, P. F., Cloning and growth of multipotential neural precursors: requirements for proliferation and differentiation, *Neuron* 10, 255–265 (1993)[43].

The authors report existence of multipotential precursor cells in E10 mouse telencephalon by culturing single cells from the brain in bFGF plus serum. The results were based on 700 cells expanded clonally for 10 days, some of which, when differentiated in the presence of bFGF, serum, and astrocyte conditioned medium, could give rise to neurons. There was no mass expansion of the cells.

Kilpatrick, T. J. and Bartlett, P. F., Cloned multipotential precursors from the mouse cerebrum require FGF-2, whereas glial restricted precursors are stimulated with either FGF-2 or EGF, *J. Neurosci.* 15, 3653–3661 (1995)[44].

The authors utilize the clonal culture system reported in the above-described reference[43] to test mitogenic efficacy of bFGF and EGF on cortical cells from E10 and E17 embryos. Again, the culture condition applies strictly to microculture in serum containing medium to demonstrate existence of different precursor cells in developing brain. There is no mass expansion, long-term culture, or systematic differentiation protocol.

Baetae, E. E., Neural stem cells for CNS transplantation. *Ann. N.Y. Acad. Sci.* 695, 285 (1993)[45].

This is a brief review paper summarizing various studies directed to isolating precursor cells and their derivatives in culture. It is somewhat outdated and most of the relevant original studies cited have been discussed above.

Bartlett, P. F. et al., Regulation of neural precursor differentiation in the embryonic and adult forebrain. *Clin. Exp. Pharm. Physiol.* 22, 559–562 (1995)[46].

This is also a brief review paper summarizing mostly previous works from the authors' laboratory in regard to their microculture studies where differentiation potentials of certain clones of precursors are tested in the presence of acidic FGF (aFGF), bFGF, serum, and/or astrocyte conditioned medium.

In addition, Sabate et al.[32] reported the culturing of a human neural progenitor with undefined differentiation capacity. Davis and Temple[6] demonstrated the existence of multipotential stem cells in cortex by co-culturing with epithelial cells for short term (less than 100 cells altogether).

However, cell differentiation could not be controlled in any of the reported studies which precluded analysis of their lineage relations and the mechanisms regulating fate choice.

The present invention provides a method for efficiently propagating the undifferentiated germinal cells, i.e., stem cells of the central nervous system (CNS), in culture and defines conditions to effectively turn the undifferentiated cells into mature cell types. These undifferentiated cells or "CNS stem cells" display the multipotential capacity to differentiate into all three major cell types of a mature brain—neurons, astrocytes, and oligodendrocytes. Moreover, the same culture conditions enable isolation, expansion, and differentiation of equivalent multipotential cells from the adult brain.

SUMMARY OF THE INVENTION

The present invention is for an in vitro culture of stem cells of the central nervous system of a mammal, a method for the in vitro culture of the stem cells, and a method for the differentiation of the stem cells.

In the in vitro culture of the stem cells of the central nervous system of a mammal, the stem cells maintain the multipotential capacity to differentiate into neurons, astrocytes, and oligodendrocytes. The stem cells can be derived from central nervous system tissue from a human, fetus or adult. Furthermore, the central nervous system tissue may be hippocampus, cerebral cortex, striatum, septum, diencephalon, mesencephalon, hindbrain, or spinal cord.

Furthermore, the stem cells can differentiate to mature neurons exhibiting axon-dendrite polarity, synaptic terminals, and localization of proteins involved in synaptogenesis and synaptic activity including neurotransmitter receptors, transporters, and processing enzymes. In addition, the stem cells retain their capacity to generate subtypes of neurons having molecular differences among the subtypes.

In the method for the in vitro culture of the stem cells, where the stem cells maintain the multipotential capacity to differentiate into neurons, astrocytes, and oligodendrocytes, cells from the central nervous system are:

a) dissociated by mechanical trituration;
b) plated at the optimal initial density of $1\times10^6$ cells (from hippocampus and septum) or $1.5\times10^6$ cells (from other CNS regions) per 10 cm plate precoated with poly-ornithine and fibronectin;
c) cultured in the complete absence of serum;
d) supplied daily with a growth factor selected from the group consisting of
 i) basic fibroblast growth factor (bFGF) at a concentration of at least 10 ng/ml,
 ii) EGF at a concentration of at least 10 ng/ml,
 iii) TGF-alpha at a concentration of at least 10 ng/ml, and
 iv) acidic FGF (aFGF) at a concentration of at least 10 ng/ml plus 1 µg/ml heparin;
e) replaced 100% of culture medium every two days with fresh medium;
f) passaged at every 4 days after plating by treating the cultured cells with saline solution and scraping the cells from the plate; and
g) replated passaged cells at $0.5\times10^6$ cells per 10 cm plate precoated with poly-ornithine and fibronectin.

The method is applicable with stems cells derived from central nervous system tissue from a human, fetus or adult. Again, the central nervous system tissue may be hippocampus, cerebral cortex, striatum, septum, diencephalon, mesencephalon, hindbrain, or spinal cord.

In the method for the differentiation of an in vitro culture of stem cells of the central nervous system of a mammal, where the stem cells maintain the multipotential capacity to differentiate into neurons, astrocytes, and oligodendrocytes, cells from the central nervous system are:

a) dissociated by mechanical trituration;
b) plated at the optimal initial density of $1\times10^6$ cells (from hippocampus and septum) or $1.5\times10^6$ cells (from other CNS regions) per 10 cm plate precoated with poly-ornithine and fibronectin;
c) cultured in the complete absence of serum;
d) supplied daily with a growth factor selected from the group consisting of
 i) basic fibroblast growth factor (bFGF) at a concentration of at least 10 ng/ml,
 ii) EGF at a concentration of at least 10 ng/ml,
 iii) TGF-alpha at a concentration of at least 10 ng/ml, and
 iv) acidic FGF (aFGF) at a concentration of at least 10 ng/ml plus 1 µg/ml heparin;
e) replaced 100% of culture medium every two days with fresh medium;
f) passaged at every 4 days after plating by treating the cultured cells with saline solution and scraping the cells from the plate;
g) replated passaged cells at $0.5\times10^6$ cells per 10 cm plate precoated with poly-ornithine and fibronectin; and
h) removed the growth factor either by rinsing the cells with saline solution or by treating with trypsin and subsequently trypsin inhibitor, and then continued to culture the cells in the serum-free medium without the growth factor.

Furthermore, differentiation may be specifically directed by adding a second growth factor to the cultured cells either before or after removing the first growth factor from the cultured cells. The second or added growth factor may be platelet-derived growth factor (PDGF), ciliary neurotropic factor (CNTF), leukemia inhibitory factor (LIF), or thyroid hormone, iodothyronine (T3).

BRIEF DESCRIPTION OF THE DRAWINGS

FIG. 2C shows a sister clone at low magnification, which have been differentiated for 6 days and immunostained with a neuron-specific antibody, TuJ1. Note the widespread and non-localized presence of TuJ1-positive neurons across the entire clone. A higher magnification view of the same cells is shown in FIG. 2D. The TuJ1-positive cells assume typical neuronal morphology. Heterogeneous morphologies in the non-neuronal TuJ1-negative cells are apparent.

Figure 3A:
FIGS. 3A–J show examples of representative clones of embryonic hippocampal cells (3A, 3C, 3E, 3G, 3I) and adult subependymal cells (3B, 3D, 3F, 3H, 3J) double-stained with combinations of antibodies to reveal different cell types within individual clones: anti-MAP2, neuronal; anti-GalC, oligodendrocytic; anti-GFAP, astrocytic. The two immunoreactions were developed sequentially and distinguished by using two distinct chromogens via alkaline phosphatase reaction (blue, indicated by arrows) versus horse radish peroxidase reaction (red, indicated by arrow heads).
Figure 3B:

The cells in FIGS. 3A and 3B were double-stained with anti-MAP2 (neuronal, arrows) and anti-GFAP (astrocytic, arrow heads) and show that bFGF-expanded clones derived from embryonic or adult brain differentiate into both neurons and astrocytes. (oligodendrocytes are unstained in this staining.)

Figure 3C:
Figure 3D:

The cells in FIGS. 3C and 3D were double-stained with anti-GalC (oligodendrocytic, arrows) and anti-GFAP (astrocytic, arrow heads) and show that bFGF-expanded clones derived from embryonic or adult brain differentiate into both oligodendrocytes and astrocytes. (Neurons are unstained in this staining.)

Figure 3E:
Figure 3F:

FIGS. 3E and 3F show clones differentiated in the presence of platelet-derived growth factor (PDGF). The cells were double stained with anti-MAP2 (neuronal, arrows) and anti-GFAP (astrocytic). Most cells were MAP2+ and only a few were GFAP+.

Figure 3G:
Figure 3H:

FIGS. 3G and 3H show clones differentiated in the presence of ciliary neurotrophic factor (CNTF). The cells were double-stained with anti-MAP2 (neuronal) and anti-GFAP (astrocytic, arrow heads). All cells were intensely GFAP+.

Figure 3I:
Figure 3J:
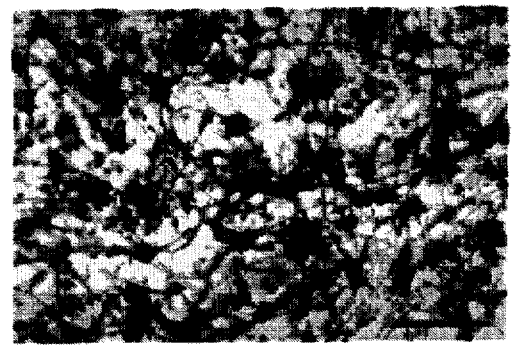

FIGS. 3I and 3J show clones differentiated in the presence of thyroid hormone, tri-iodothyronine (T3). The cells were double-stained with anti-GalC (oligodendrocytic, arrows) and anti-GFAP (astrocytic, arrow heads). GFAP+and, particularly, GalC+ cells increased. MAP2+ cells decreased (Table IV).

Figure 4:
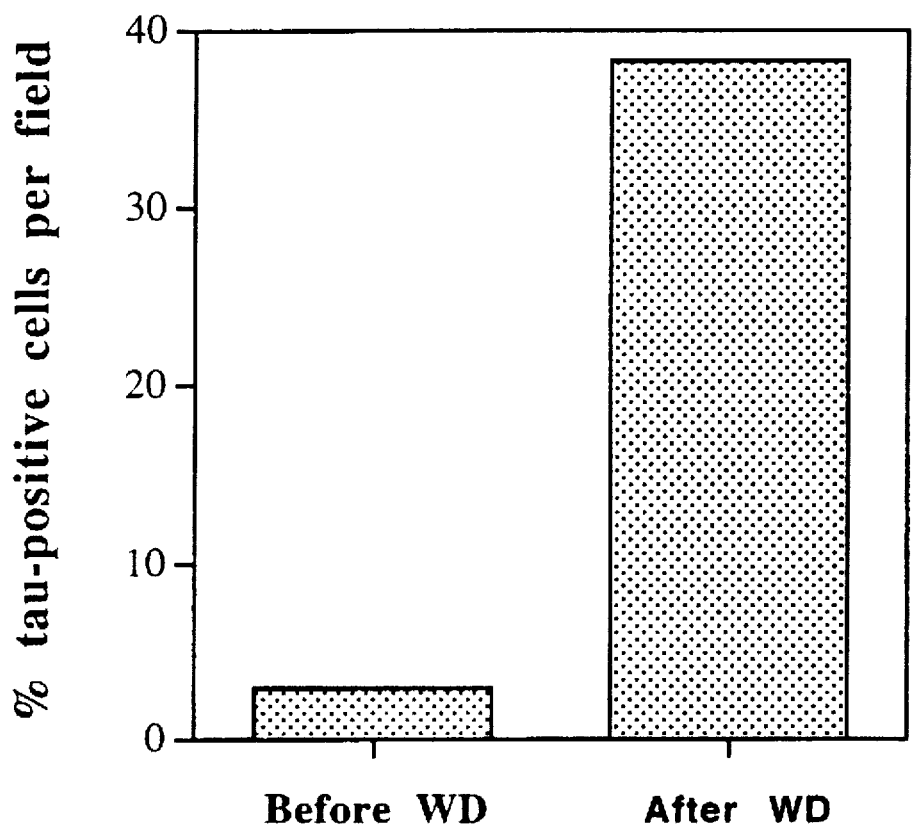

FIG. 4 shows the differentiation of human CNS stem cells into neuron in high density culture. bFGF-expanded CNS cells at high density were differentiated by withdrawal of bFGF ("WD"). The number of neurons expressing tau protein was determined by immunocytochemistry in culture during the expansion phase ("Before WD") versus after differentiation ("After WD"). The dramatic increase in post-mitotic neurons only after the withdrawal of bFGF indicates that they were generated from the dividing stem cells.

FIGS. 5A–F show human stem cells stained with human-specific anti-tau antiserum (Chemicon) which identify neurons. Proliferating human CNS stem cells in high density culture do not express tau protein, a neuronal marker (FIG. 5A). After 6 days of differentiation, however, many cells with typical neuronal morphology express high level of tau protein (FIG. 5B). In order to further demonstrate that these neurons have indeed derived from dividing stem cells, the stem cells were labeled with 10 μM bromodeoxyuridine (BrdU), an indicator of mitosis, for 24 hours just prior to the bFGF withdrawal. They were then differentiated for 6 days, double stained with human specific anti-tau antiserum (FITC, green) and anti-BrdU antibody (Rhodamine, red). FIG. 5C shows a high magnification view of subsequent tau-positive neurons as seen through FITC fluorescence. FIG. 5D shows the same field of view as in FIG. 5D but seen through rhodamine fluorescence to reveal BrdU-positive nuclei. Most tau-positive neurons are also positive for BrdU, demonstrating that they were derived from mitotic stem cells before the bFGF withdrawal.

In order to further demonstrate multi-potentiality of human CNS stem cells, they were cultured at clonal density as described for rodent cells. FIG. 5E shows a typical clone at low magnification, which has been expanded from a single cell for 20 days, subsequently differentiated for 12 days, and immunostained with the neuron specific, anti-MAP2 antibody. Neurons are abundant in the clone. FIG. 5F shows a higher magnification view of the clone in FIG. 5E to indicate that the MAP2-positive cell are of typical neuronal morphology.

Figure 6A:
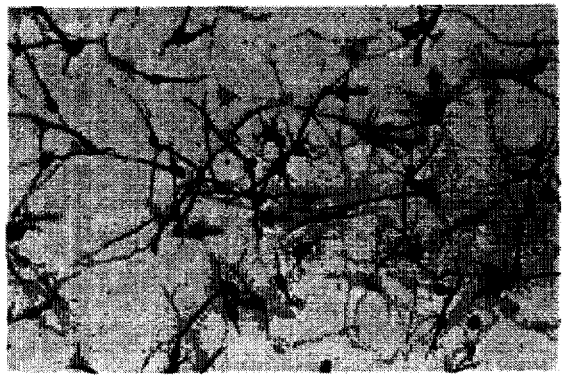
Figure 6B:
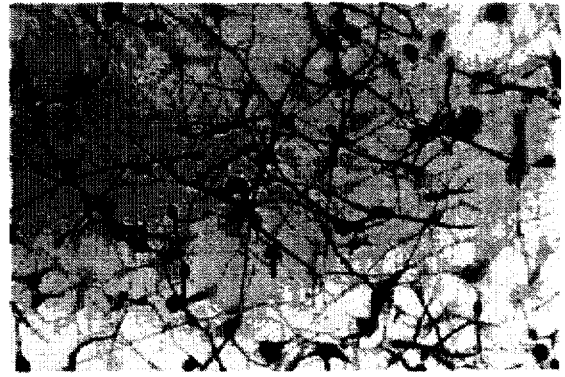
Figure 6C:
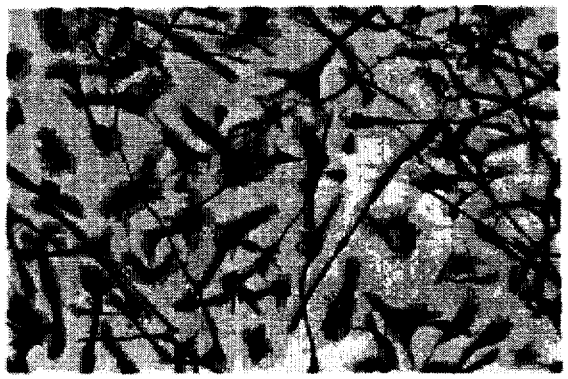
Figure 6D:
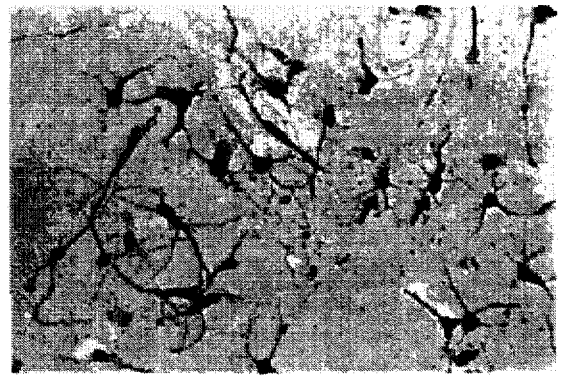

FIGS. 6A–D demonstrate directed differentiation of human CNS stem cells. Human CNS stem cells after 16 days of expansion were grown clonally for an additional 20 days and then differentiated in the presence or absence of single factors, PDGF (10 ng/ml), CNTF (10 ng/ml), or T3 (3 ng/ml). FIG. 6A shows a untreated control clone, with approximately 50% MAP2-positive neurons (arrows) and 2–10% GFAP-positive astrocytes (arrow heads). FIG. 6B shows a PDGF-treated clone, where 75% of cells are MAP2-positive neurons (arrows) and 2–10% GFAP-positive astrocytes (arrow heads). FIG. 6C shows a CNTF-treated clone, where 85% are GFAP-positive astrocytes (arrow heads) and only 9% MAP2-positive neurons (arrows). FIG. 6D shows a T3-treated clone with increased number of O4- and/or GalC-positive oligodendrocytes (arrows) and of GFAP-positive astrocytes (arrow heads).

FIGS. 7A–7I show that a large number of mature neurons with correct axon-dendritic polarity and synaptic activity can be obtained routinely from long-term expanded CNS stem cells. Hippocampal stem cells from E16 rat embryos were expanded in culture for 16 days and through 4 passages. Just before the last passage, rapidly dividing cells were labeled with 10 μM BrdU for overnight, passaged by using trypsin, and plated onto chamber slides. Cells were maintained for 21 days to allow constitutive differentiation and maturation of neurons. Subsequently, the extent of maturation and neuronal subtypes generated were analyzed by immunocytochemistry.

Figure 7A:

FIG. 7A: Neurons stained with TuJ1 antibody viewed at low magnification (100×) to illustrate that production of neurons is efficient.

Figure 7B:

FIG. 7B: Typical morphology of neurons revealed by TuJ1 antibodies (400×).

Figure 7C:

FIG. 7C: Typical morphology of neurons revealed by MAP2 antibodies (400×).

Figure 7D:
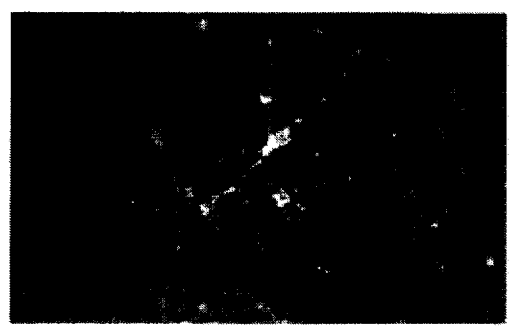

FIG. 7D: Neurons stained with synapsin antibody. Only mature neurons containing synaptic vesicles are stained.

Figure 7E:
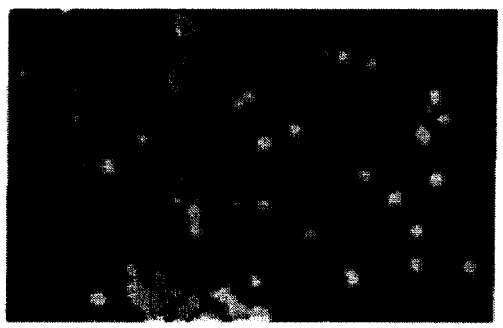

FIG. 7E: BrdU staining. All cells in the culture, neurons and glia, are labeled with BrdU.

Figure 7F:

FIG. 7F: Synapsin and BrdU double staining. Mature synapsin-positive cells are also BrdU-positive, demonstrating that they are derived from mitotic stem cells in culture.

Figure 7G:

FIG. 7G: Punctate anti-synapsin antibody staining marks the presynaptic axon terminals specifically in large mature neurons.

Figure 7H:
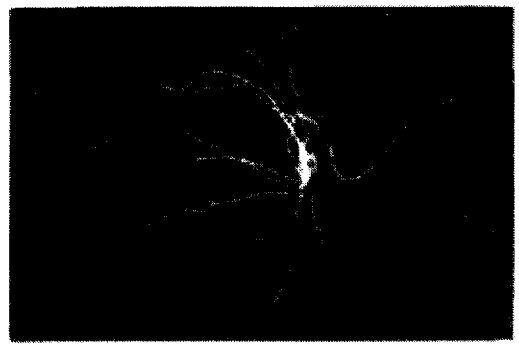

FIG. 7H: The synapsin-positive structures are closely apposed to dendritic processes revealed by MAP2 antibody staining.

Figure 7I:
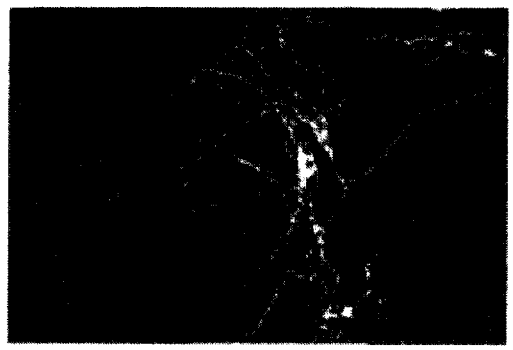

FIG. 7I: MAP2 and synapsin proteins are closely associated but not co-localized, suggesting presynaptic-postsynaptic interaction.

FIG. 8 shows that stem cell-derived neurons express various neurotransmitter receptors and transporters expected to be involved in synaptic transmission as detected by RT-PCR. Long-term expanded stem cells derived from E16 rodent cortex were differentiated for 14 days and harvested to prepare RNA. Undifferentiated stem cells were also prepared in order to compare differentiation-specific induction. RNA from a whole brain of adult rat was used as a positive control. Primers specific for NMDA (N-methyl-D-aspartate) and AMPA (α-amino-3-hydroxy-5-methyl-4-isoxazole proprionic acid) families of glutamate receptor subtypes as well as for various GABA transporters were used. Note especially the specific induction of NMDA R1, AMPA R1 and AMPA R2 receptors in differentiated cells.

DETAILED DESCRIPTION OF THE INVENTION

In this application, conditions are defined which permit mass expansion up to $10^9$ fold in culture and controlled differentiation of multipotential CNS stem cells from the embryonic and adult brain of mammals. In both cases, clones derived from single cells differentiate into neurons, astrocytes, and oligodendrocytes. Addition of single factors can dramatically shift the proportion of cell types within a clone.

The procedure for isolating, propagating, and differentiating the CNS stem cells are given in detail below. The procedure contains four essential steps that must be followed in concert for successful isolation and differentiation of the CNS stem cells. The four essential steps are as follows:

(1) The initial dissociation of cells from tissue is done by mechanical trituration and not by enzymatic digestion. With adult tissue, it is necessary to first enzymatically digest the tissue and then dissociate the cells from the tissue by mechanical trituration.

Trituration means gentle agitation of cell aggregates caused by fluid movement occurring during repetitive pipetting action by which individual cells become loose and dissociated from neighboring cells. Trituration is done in a saline solution free of divalent cations whose absence aids break-up of interactions among cell-adhesion proteins on cell surface. Rapidly dividing stem cells in the ventricular zone are only weakly adherent and simply removing the divalent cations from the medium and gentle agitation by pipetting are sufficient to dissociate the tissue into mostly single cells. The cells are then cultured in the complete absence of serum. Even a brief exposure to serum deleteriously affects the differentiation capacity of the stem cells so that they are no longer able to differentiate into neurons and oligodendrocytes. Precoating the plates with poly-L-ornithine and fibronectin facilitates the adhesion of the cells to the plates.

(2) The CNS stem cells display an innate property to differentiate spontaneously, which reflects a regulatory mechanism controlling cell cycle depending upon the free concentration of growth factor, the mitogen. In order to suppress the differentiation of the stem cells into other cell types and to maintain homogeneity, the growth factor must be supplied daily at a concentration of 10 ng/ml or higher. The growth factor can be selected from (1) basic fibroblast growth factor (bFGF), (2) EGF, (3) TGF-alpha, or (4) acidic FGF (aFGF). If acidic fibroblast growth factor is selected, heparin at a concentration of 1 µg/ml must also be supplied.

(3) Even a continuous supply of bFGF or other selected growth factor is insufficient to inhibit differentiation if the culture is allowed to reach a critical density of greater than approximately 50%. This is most likely because of yet undefined endogenous factor(s) secreted by the dividing cells themselves which antagonize the action of bFGF. Thus, in order to remove such factors from the culture and to reduce cell-cell interaction as much as possible, the cells must be passaged frequently at every 4 days after plating, and replating should be done at low density of approximately $0.5 \times 10^6$ per 10 cm plate, i.e., in the range of $1 \times 10^2$ to $1 \times 10^6$ cells per 10 cm plate, precoated with poly-ornithine and fibronectin.

(4) Passaging the cells by trypsin results in proteolytic removal of a bFGF receptor component and disables the mitogenic effect of bFGF. The turn-over rate of the receptor is sufficiently slow during which period the cells fail to recognize the mitogen and activate the differentiation pathway. In order to circumvent this process, the cells are treated with Hank's buffered saline solution (HBSS) to remove divalent cations in the culture which disrupts the ionic interactions between the cadherins and the integrins on the cell surface and extracellular matrix proteins on the culture plate, causing the cells to round up. At this point the stem cells can be scraped from the plate with a scraper without damaging the cells. Other cells in culture maintain tightly bound to the plate and scraping eliminates them, thus allowing effective selection of rapidly dividing undifferentiated stem cells.

Differentiation of the CNS stem cells is achieved by simply removing the mitogen, bFGF or other selected growth factor, from the medium. Specification of the cell types, i.e., neurons, oligodendrocytes, and astrocytes, occurs constitutively. In order for the effective controlled differentiation, the cells must be in a homogeneous state which can be achieved by following steps 1–4, above.

These procedures yield a culture system for obtaining a homogeneous population of the CNS stem cells that can be differentiated into neurons, oligodendrocytes, and astrocytes with control and efficiency. The highlights of the features of this system are:

(1) production of a large number of the CNS stem cells with the potential to form many different neuronal subtypes, oligodendrocytes, and astrocytes that can be transplanted into a brain;

(2) controlled differentiation in vitro under serum-free conditions which allows the search for novel growth factors and cytokines;

(3) rapidly dividing cells accessible to genetic manipulation for introduction of foreign genes;

(4) generation of mature neurons in vitro suitable for genetic and pharmacological screening; and (5) direct derivation of intermediate precursor cells from the stem cells for enrichment of a single population of cells.

The isolation of the CNS stem cells in the above-described manner further permits directed differentiation of the cells by treating them with specific growth factors. One practical significance of this directed differentiation to biotechnology is that a single cell type can be enriched in vitro. Thus, a novel application of previously discovered growth factors PDGF[37] (platelet-derived growth factor), CNTF (ciliary neurotrophic factor), and T3 (thyroid hormone, tri-iodothyronine) would be to direct the CNS stem cells to generate neurons, astrocytes, and oligodendrocytes, respectively. Another practical significance, especially for PDGF, is that PDGF-induced neurons appear to be actually neuronal progenitors that can further proliferate and expand in culture by PDGF. These cells differentiate only to neurons or to neurons and oligodendrocytes and differ from the stem cells. Isolation of neuronal progenitors from mammalian CNS by PDGF has not been described previously.

EXAMPLES

1. Isolation of CNS Stem Cells from Embryonic Rat Brain

Rat embryonic hippocampus (gestation day 16; day of conception is day 1, Taconic Farm) were dissected in Hank's buffered saline solution (HBSS) and dissociated by brief mechanical trituration in HBSS. The cells were collected by centrifugation and resuspended in a serum-free medium containing DMEM/F12, glucose, glutamine, sodium bicarbonate, 25 µg/ml insulin, 100 µg/ml human apotransferrin, 100 nM progesterone, 10 µM putrescine, 25 nM sodium selenite, pH 7.2[8], plus 10 ng/ml recombinant human basic fibroblast growth factor[12] (bFGF; R&D Inc.).

$1 \times 10^6$ cells were plated per 10 cm plastic tissue culture plate precoated with 15 µg/ml poly-L-ornithine and 1 µg/ml bovine plasma fibronectin (Gibco). bFGF was added daily and media change was every 2 days. Cells were passaged at 50% confluence (4 days after initial plating) by briefly incubating them in HBSS and scraping with a cell scraper.

Cells with multipotential capacity were found throughout the developing neuroepithelium. Under identical culture conditions, similar cells could be prepared from other regions of the developing CNS including cerebral cortex, striatum, septum, diencephalon, mesencephalon, hindbrain, and spinal cord. From E14 cortex and striatum and E16 hippocampus, approximately 70% of acutely dissociated cells responded to bFGF within 2 days of plating by undergoing mitosis.

2. Propagation of CNS Stem Cells from Embryonic Rat Brain a) Mass Expansion

Hippocampal cells isolated from embryonic rat brains were expanded by daily addition of basic fibroblast growth factor (bFGF) in serum-free medium. Continuous supply of bFGF was important to repress differentiation and to maintain a homogeneous population of rapidly dividing cells expressing nestin, an intermediate filament protein characteristic for CNS precursor cells[13,14]. Less than 1% of the cells expressed the astroglial marker GFAP or the oligodendroglial markers, O4 and GalC.

The cells were passaged 4 days after plating during which time cell number increased rapidly with an average cell doubling time of approximately 24 hours. Passaged cells were replated at $0.5 \times 10^6$ cells per 10 cm plate and were allowed to propagate further. Cells could be passaged up to five times in this manner for a total of 20 days in vitro during which time a yield of $2^{20}$ cells could be ideally expected. After this time period, the mitotic rate of the cells declined rapidly and the cells gradually lost their multipotential capacity, exhibiting glial characteristics and unable to differentiate into neurons.

Large numbers of cells from cortex, striatum, and septum isolated from embryos of 12–18 days of gestation could also be expanded in mass culture in the same manner. The time course of the expansion was similar to that of hippocampal cells. Continuous expansion was again limited by the constitutive loss of multipotentiality after about 20 days of cell division. Thus, this regression appears to be a characteristic property of CNS stem cells.

b) Clonal expansion

No simple antigenic marker is available which uniquely identifies multipotential stem cells from other precursors in vitro. Identity of a precursor population can only be ascertained by the cell's differentiation capacity. The conditions defined for mass culture in this application also permitted clonal expansion where cells were plated at extremely low cell density so that single cells were well isolated.

Differentiation capacity of the cells expanded in mass culture was assessed at each passage by plating 200 cells per 10 cm plate and cultured under conditions as described above. Within 24 hours of plating, well isolated single cells were marked with a 3 mm ring (Nikon) on the bottom of the plate. Initial viability of the marked single cells was 5–10% and each plate typically yielded 10–20 marked clones. Only a single cell resided in each circle. The subsequent population of cells within each circle are progeny of that single cell. Clones were expanded for up to 10 days (500–2000 cells). Average double time was approximately 24 hours.

3. Differentiation and Analysis of CNS Stem Cells from Embryonic Rat Brain

Developmental potential of expanded cells was tested by directly differentiating the cells. Withdrawal of bFGF initiated differentiation within 24 hours. To initiate differentiation of high density cells, rapidly dividing cells, which had been in culture for 12 days and passaged three times, were incubated for the last 24 hours with 10 µM BrdU (bromodeoxyuridine) prior to passaging. 80–85% of the cells incorporated BrdU. The cells were harvested either by scraping or by using trypsin followed by soybean trypsin inhibitor in the serum-free medium. They were plated in duplicate at 40,000 cells/cm$^2$ into multi-well chamber slides (LabTek) precoated with poly-L-ornithine and fibronectin, and cultured in the serum-free medium without bFGF. At indicated times, the cells were fixed and stained with various antibodies according to standard procedure.

Immunopositive cells were counted under 400× magnification. At least five fields with a total cell number greater than 1,000 per sample were counted. Results shown (FIG. 1A) are cell counts averaged from two experiments. Antibody reagents used were: anti-nestin antiserum; monoclonal anti-MAP2 (clone HM-2, Sigma) and anti-tau antiserum (Sigma), monoclonal anti-neurofilament L and M (clones NR4 and NN18, Boehringer-Manheim), anti-beta tubulin type III (TuJ1), monoclonal anti-GFAP (ICN), A2B5 (ATCC), O4, and anti-galactocerebroside (GalC).

Figure 1A:
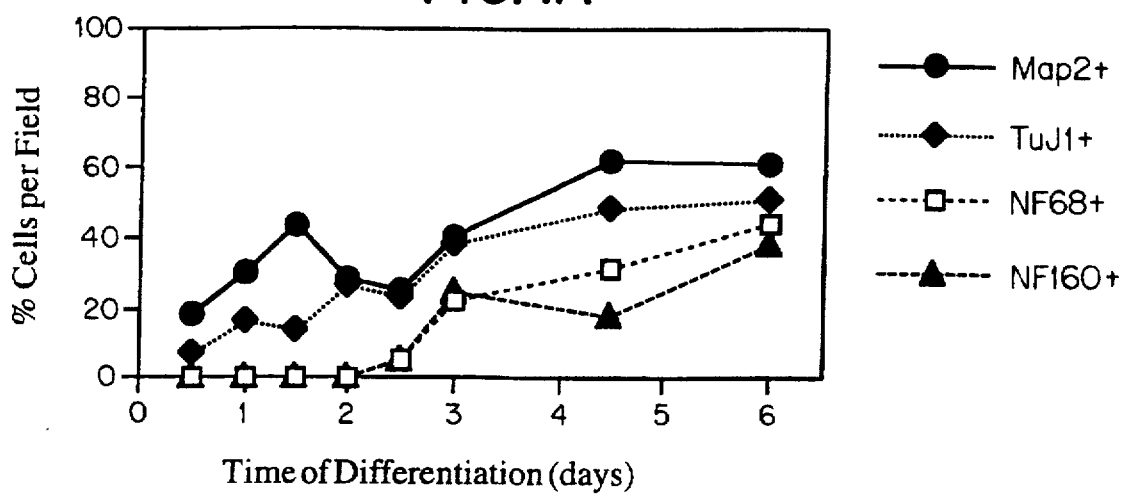
FIG. 1A shows the controlled differentiation of CNS stem cells at high density. Rapidly dividing nestin-positive precursor cells were labelled with BrdU during the last 24 hours of proliferation. Differentiation was then initiated by withdrawal of bFGF (day 0) and continued for up to 6 days. At indicated times, cells were fixed and stained for BrdU and neuronal antigens. Ratios of cells double-stained for BrdU and each neuronal antigen to total BrdU positive (BrdU+) cells are shown. Up to 50% of BrdU+ cells expressed neuronal antigens and their expression was time-dependent. MAP2 positive (MAP2+), filled circle; TuJ1 positive (TuJ1+), grey diamond; neurofilament L positive (neurofilament L+), open square; neurofilament M positive (neurofilament M+), filled triangle.

Over a 6 day period, there was a progressive increase in the number of cells expressing several well established neuron-specific antigens, including MAP2a, b and c, beta tubulin type 3 (TuJ1), tau, and neurofilaments L, M, and H (FIG. 1A). Up to 50% of the cells expressed the neuronal antigens and exhibited complex neuronal morphology. The remaining cells expressed GFAP, GalC/O4, or nestin. While neurons and glia have been observed previously in expanded culture, these examples are the first to establish that the differentiation of proliferating precursor cells can be initiated at a precise time point and that multiple cell types arise rapidly. These conditions permit large scale lineage analysis in vitro.

To determine if the precursor population contains separate committed progenitors that independently give rise to neurons and glia, rapidly dividing cells were plated at clonal density (200 cells per 10 cm plate) and well-isolated single cells were marked with 3 mm diameter circles. 5–10% of the marked single cells survived and proliferated with a doubling time of 24 hours to generate clones. After various periods of expansion (clone sizes ranging from $2^4$ to $2^{10}$ cells), differentiation of clones was initiated by washing the plates once with HBSS and culturing in the same medium but in the absence of bFGF (FIG. 2).

For subcloning (data shown in Table II), the clonal plates were washed and briefly left in HBSS until the cells rounded up. Clones of 500–2000 cells were picked in 50 µl volume with an adjustable pipetter while viewing through a microscope. Each clone was replated in a 10 cm plate and single cells were marked and cultured as before.

Cell types within clones were analyzed during the first six days of differentiation by double-staining with combinations of cell-type specific antibodies that react with mutually exclusive cells:

neurons=MAP2+, tau+, TuJ1+, neurofilament L+, or neurofilament M+;

astrocytes=GFAP+; and oligodendrocytes=O4+ or GalC+.

Double staining was done sequentially using a commercial kit (Zymed) according to the manufacturer instructions. For oligodendrocyte staining, cells fixed with 4% paraformaldehyde were stained first for the cell-surface antigens O4 or GalC without permeabilization. The first antibody was developed with alkaline phosphatase reaction (blue) and the second with peroxidase reaction (red) (Zymed).

As in high density culture, by six days, 50% of the cells in a clone expressed neuronal antigens including MAP2, tau, and beta tubulin type III (Table I, FIG. 3A and C). In Table I, clones of hippocampal precursor cells were expanded, differentiated, and analyzed as described above. A partial list of typical clones are presented above. Total number of cells (clone size) and cells stained positive for cell-type specific antigens are shown. Their relative proportion is given in percentage in parenthesis. A total of 48 clones was quantified from 4 different passages in 6 separate experiments. Total Average indicates the average composition of each cell types in the 48 clones.

Neurofilament expression was delayed under these conditions. On average, 8% of the cells in a clone were GalC+ and had typical oligodendrocyte morphology. An additional 8% expressed GFAP and displayed a characteristic astrocytic morphology. The remaining cells were unstained by any of the antibodies specific for differentiated cell types but reacted with A2B5 and/or anti-nestin antibodies. A maximum of 20% of the cells died during differentiation. Identical results were obtained whether clones were obtained from acutely dissociated cells with no prior passage or from cells after 4 passages (26 days in vitro).

Cells with multipotential capacity were found throughout the developing neuroepithelium. Under identical culture conditions, similar cells could be prepared from other regions of the developing CNS including cerebral cortex, striatum, septum, diencephalon, mesencephalon, hindbrain, and spinal cord. When clonally expanded, almost all of the clones contained multiple cell types defined by both morphology and antigen expression with neurons constituting 50% of the clone.

Figure 1B:
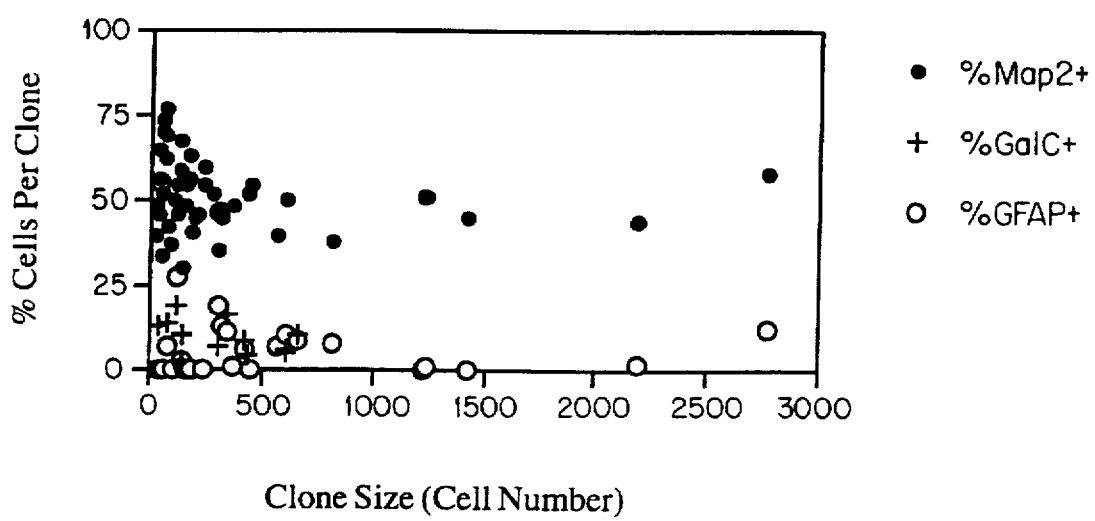
FIG. 1B shows proportions of MAP2+ neurons (●), GalC+ oligodendrocytes (+), and GFAP+ astrocytes (○) in differentiated clones. Clones of various sizes ranging from 39 cells to 2800 cells were differentiated for 6 days and analyzed for two cell types per clone by double immunohistochemistry. A partial list is given in Table I and immunostaining shown in FIG. 3. The number of neurons increased with increasing clone size, constituting 50% of the clone.

Proliferating clones of the multipotential cells contained uniform morphology and patterns of antigen expression. Yet, the separation of neuronal and non-neuronal morphologies occurred rapidly within 24 hours and only after the mitogen withdrawal. The early neurons were evenly distributed throughout the clone without obvious polarity or localization, suggesting the absence of committed neuronal progenitors during clonal expansion. Moreover, the number of neurons increased linearly with increasing clone size and reproducibly constituted 50% of the clone (FIG. 1B).

In order to further determine if expanding clones consisted of proliferating committed progenitors, clones were picked and replated again. 10–15% of the cells gave rise to second generation clones. Again, all of the subclones contained neurons, astrocytes, oligodendrocytes, and unstained cells (Table II). More specifically, cell type composition of subclones obtained from three independent clones, HI6, HI8, HI19, are shown in Table II. A total of 84 subclones was quantified from 13 independent parental clones in two separate experiments. Only a partial list is presented. Total Average indicates the average composition of each cell type from the 84 subclones. No subclone consisted of only one cell type. These data indicate that the multipotential precursors undergo symmetric divisions to generate daughter cells with multipotential capacity.

4. Isolation, Propagation, Differentiation, and Analysis of CNS Stem Cells from Adult Rat Brain The subependymal layer of adult rat brain contains mitotic nestin positive cells that could be expanded in aggregate culture in the presence of epidermal growth factor (EGF) but not bFGF[15]. Some of the cells in aggregates showed neuronal and astrocytic properties. To more fully define their developmental capacity, the mitotic population (1% of 1×10$^5$ cells/brain) lining the lateral ventricle of adult rat striatum was expanded in the presence of bFGF and compared to the embryonic precursors. Forebrain slices from 250 g adult rat brains (10–20 per experiment) were prepared and the subependymal region of striatum lining the lateral ventricles were cut out under microscope in oxygenated HBSS. The cells were dissociated by incubating minced tissues at room temperature for 10 minutes with trypsin (1 mg/ml), hyaluronidase (0.7 mg/ml), and kynurenic acid (0.2 mg/ml) in oxygenated HBSS. They were washed once in HBSS with 0.7 mg/ml ovomucoid and 0.2 mg/ml kynurenic acid, resuspended, and mechanically triturated in the same solution. Dissociated cells were recovered by centrifugation and cultured in the serum-free medium plus bFGF (10 ng/ml) as described for the embryonic cells.

The morphology and growth characteristics of the nestin-positive adult cells were similar to those of embryonic cells. Following bFGF withdrawal, marked clones differentiated into multiple cell types expressing MAP2, TuJ1, GFAP, and GalC (FIG. 3B and D). Strikingly, the same high proportion of neurons were found in differentiated clones of adult cells as in the embryonic clones (Table III). More specifically, Table III shows the cell type composition of differentiated clones derived from adult subependymal cells. 23 clones from three independent experiments were quantified.

5. Isolation, Propagation, Differentiation, and Analysis of CNS Stem Cells from Embryonic and Adult Rat Brains Acutely dissociated cells from various regions of embryonic brain were cultured in the presence of either EGF (20 ng/ml) or bFGF (10 ng/ml) under identical conditions as described above. Acutely dissociated adult cells were prepared as described above and cultured under identical condition as the embryonic cells. The possible effect of initial cell density on the mitogenic response was tested by varying the initial cell density from 1×10$^4$ to 2.5×10$^6$ per plate. At low density, efficiency of colony formation was measured; at high density, BrdU+/nestin+ mitotic cells per field were counted. EGF- and bFGF-expanded colonies were also differentiated by withdrawing the mitogens and cell types analyzed as described above.

Figure 1C:
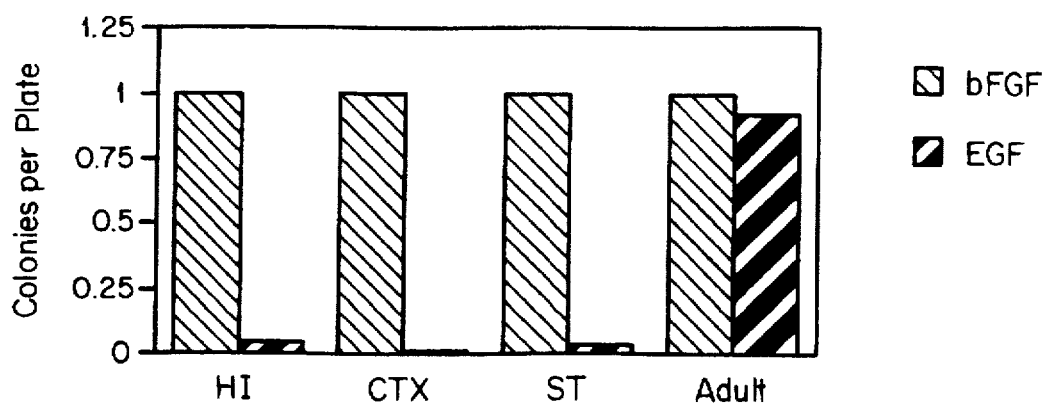
FIG. 1C shows a comparison of the mitogenic efficacies of epidermal growth factor (EGF) and basic fibroblast growth factor (bFGF). Cells (initial density of $1\times10^4$ per plate) acutely dissociated from E16 hippocampus (HI), E14 cortex (CTX) and striatum (ST), and adult subependymal layer (Adult) were expanded with either EGF (20 ng/ml) or bFGF (10 ng/ml). Colonies arising after 10 days of expansion were stained for nestin, an intermediate filament protein characteristic for CNS precursor cells[13,14]. Relative number of colonies averaged from at least 2 experiments for each region are shown (bFGF=1). Twenty- to fifty-fold more nestin+ colonies per plate were present when embryonic cells were grown in bFGF (dotted bar) than in EGF (striped bar). At high densities ($1\times10^6$ and $2.5\times10^6$), bFGF condition gave 10-fold higher BrdU+/nestin+ cells than EGF. Both growth factors were equally mitogenic for the adult cells. When EGF- and bFGF-expanded clones were differentiated, neurons and oligodendrocytes were found in similar quantities; however, EGF-expanded clones gave rise to significantly higher number of GFAP+ astrocytes.
Figure 2A:
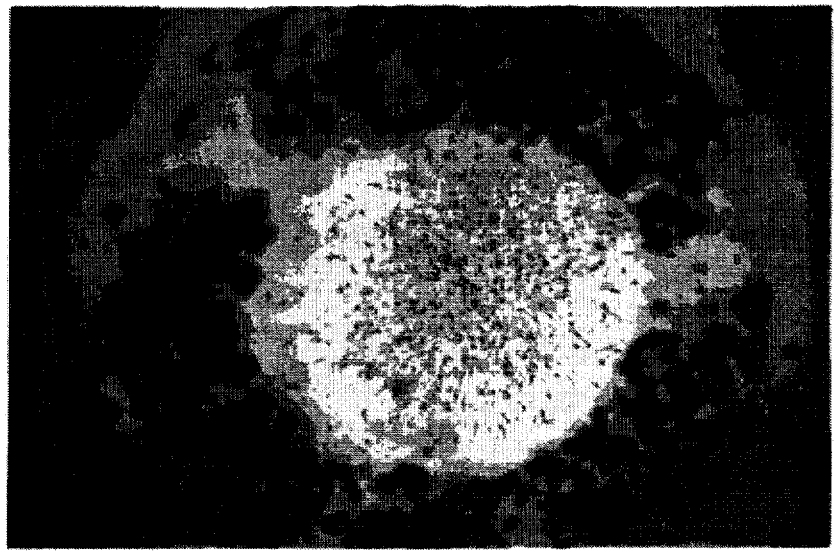
FIGS. 2A–D show a typical clone of CNS stem cells. Cells were marked by a circle on the plate within 24 hours of plating before the first mitosis and then expanded up to 10 days (FIG. 2A). Higher magnification view of another clone before differentiation, immunostained with anti-nestin antibody, is shown in FIG. 2B. Note the homogeneous radial morphology of the nestin-positive cells consistent with the nestin-positive morphology in neuroepithelium in vivo.
Figure 2B:
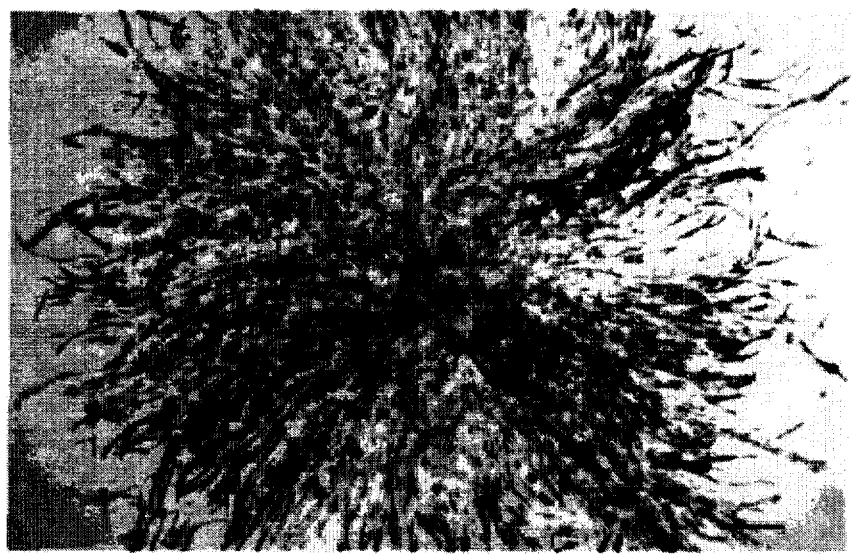
Figure 2C:
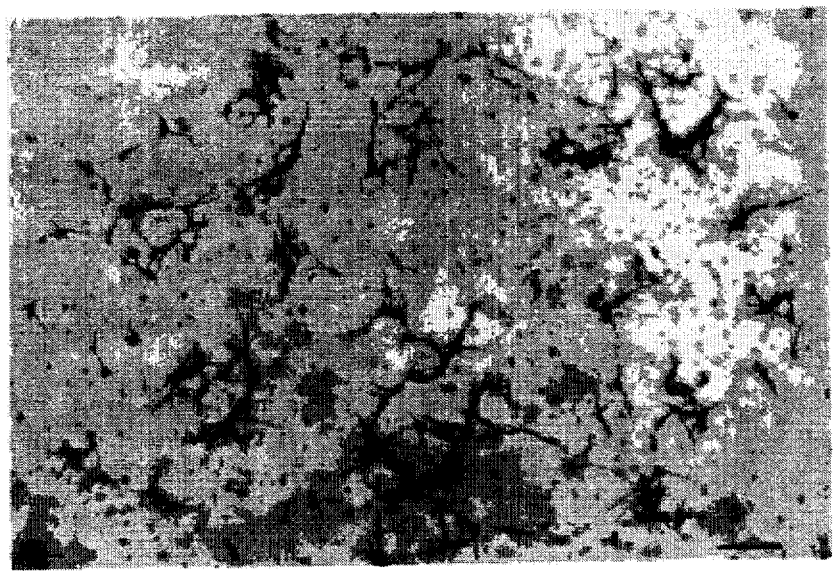
Figure 2D:
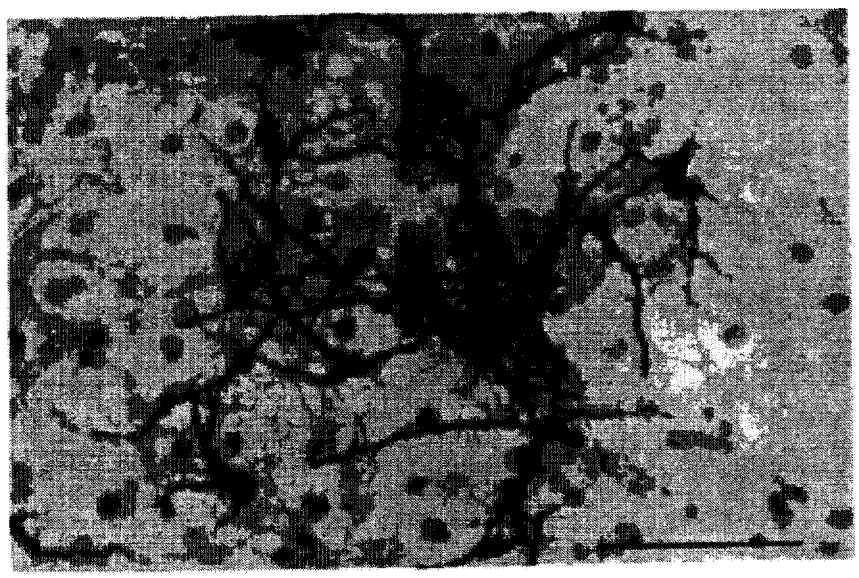

Under the culture conditions of these examples, EGF was an equally effective mitogen as bFGF for adult cells (FIG. 1C) and, when clones were differentiated, they gave rise to all three cell types. EGF-expanded embryonic clones, with and without passage, also differentiated into all three cell types. Unlike the adult cells, however, EGF was at least 10-fold less effective than bFGF as a mitogen for the embryonic cells from several different regions, regardless of initial cell density (FIG. 1C). Thus, with the exception of the proliferative effects of EGF, these data reveal that the multipotential cells from embryonic and adult CNS are remarkably similar. TGFα (10 ng/ml) was also a mitogen for the multipotential cells and was indistinguishable from EGF, while aFGF (10 ng/ml) in the presence of heparin (1 μg/ml) mimicked the effects of bFGF.

6. Directed Differentiation of CNS Stem Cells from Embryonic and Adult Rat Brain The clonal analysis suggests that the multipotential precursors are not committed prior to mitogen withdrawal and thus extracellular signals may regulate cell type determination. We tested whether the proportion of the cell types generated within a clone could be influenced by growth factors and cytokines either during proliferation or differentiation.

Influence of growth factors on cell type specification was tested by adding them to the culture two days before the withdrawal of bFGF and during the 6 days of differentiation. Factors were added daily and medium was changed every 2 days. At the end of the 6 days, the clones were analyzed for cell type composition by double-staining as described above. Final concentrations of the factors were 10 ng/ml PDGF-AA, -AB, or -BB, 10 ng/ml CNTF, and 3 ng/ml T3.

In embryonic clones, the proportion of neurons increased significantly in the presence of PDGF (10 ng/ml, -AA, -AB, or -BB) during the differentiation. Up to 80% of the cells were neuronal with MAP2, tau, TuJ1, or NF-M expression, and fewer cells expressed O4, GalC, and GFAP (FIG. 3E and F, Table IV). More specifically, Table IV shows the average clonal composition of each cell type obtained when clones were differentiated for 6 days either in the absence (Untreated) or presence of different factors. Clonal plates were prepared from cells after 0–3 passages. Clone size ranged from 17 to 5336 cells. Differentiated cell types were analyzed as described above.

The cells expressing the neuronal antigens showed a less mature morphology under these conditions. When treated with ciliary neurotrophic factor (CNTF), clones gave rise almost exclusively to astrocytes (FIG. 3G and H, Table IV). Remarkably, less than 1% of the cells were MAP2-positive in this condition. The CNTF-treated cells were intensely GFAP-positive and all showed a flat, astrocytic morphology. LIF showed identical effects as CNTF.

Thyroid hormone, tri-iodothyronine (T3), influenced the differentiation of the multipotential precursors toward a mixed glial fate (FIG. 3I and J, Table IV). Astrocytes and oligodendrocytes were both increased 3-fold and there was a marked decrease in the proportion of neurons. As in the untreated clones, GalC- and O4-positive cells showed characteristic oligodendrocyte morphologies. The clones were of similar size in all the experiments and numerical analysis of dead cells showed that selective cell death cannot account for the changes in the proportion of cell types. Similar results were obtained with multipotential stem cells from embryonic cortex and striatum. Furthermore, the multipotential cells derived from subependymal layer of the adult brain showed quantitatively similar differentiation responses to PDGF, CNTF, and T3 (FIG. 3, Table IV). This emphasizes the general nature of these pathways.

Other factors that were tested during this study and showed no significant instructive effect on cell type determination were: NGF, NT-3, BDNF, TGFb1, IL1b, IL2–11, G-CSF, M-CSF, GM-CSF, oncostatin M, stem cell factor, erythropoietin, interferon gamma, 9-cis and all-trans retinoic acid, retinyl acetate, dexamethasone, and corticosterone.

7. Isolation, Expansion, Differentiation, and Analysis of CNS Stem Cells from Human Fetal Brain Tissues from various regions of human fetal brains were obtained from fetuses of 45 to 114 days of gestation periods. The tissues were dissociated in HBSS by mechanical trituration as described above. Cells were collected by centrifugation, resuspended, plated at $1 \times 10^6$ cells per 10 cm plate, and expanded in the serum-free medium plus 10 ng/ml bFGF under conditions identical to those described for rodent fetal CNS stem cells above.

Approximately 25–50% of the human cells depending upon the age and the region had CNS stem cell morphology and responded to bFGF by rapid cell division. Human CNS stem cells were expanded in culture for up to 36 days. Average doubling time was approximately 48 hours, which contrasts with the rodent counterpart with 24 hour doubling time. Upon withdrawal of bFGF, the differentiation of human fetal CNS stem cells occurred rapidly and multiple cell types arose. In high density culture, the cells were differentiated for up to 13 days and subsequent cell types present were analyzed by immunocyto-chemistry as described for rodent cell culture. Before differentiation by bFGF withdrawal, few tau-positive neurons were present in the culture (FIG. 4). In contrast, after the bFGF withdrawal, up to 40% of the bFGF-expanded human fetal brain cells in mass culture were neurons immunoreactive with human-specific anti-tau antiserum. A majority of the tau-positive neurons in culture could be labeled with BrdU (bromodeoxyuridine), the indicator of mitosis, within 24 hours prior to the bFGF withdrawal (FIG. 5C and D). This result demonstrates that the culture conditions defined for rodent CNS stem cells applies equally well for efficient expansion and differentiation of human CNS stem cells to generate large numbers of neurons in culture.

In order to further analyze the multi-potentiality of the human fetal CNS stem cells in mass culture, dividing cells were plated at clonal density (100–200 cells per 10 cm plate) and further expanded for 20 days (clone size=$2^{10}$). Subsequently, clones were differentiated by withdrawing bFGF and analyzed for cell types immunoreactive for neuron-, astrocyte-, or oligodendrocyte-specific antibodies. Almost all of clonally expanded human fetal cells differentiated to give rise to all three cell types—neurons, astrocytes, and oligdendrocytes (FIG. 5E and F). As with rodent stem cells, MAP2-positive neurons comprised approximately 50% of the clone (Table V). The remaining cells were of large elongated glial morphology. Approximately 10% of the cells expressed mature astrocytic antigen, GFAP, and about 2% expressed oligodendrocytic antigens O4 or galactocerebroside (GalC) (Table V). This clonal analysis thus demonstrates that the culture system described here permits efficient isolation, mass-expansion, and differentiation of multipotential stem cells from human fetal CNS.

8. Directed Differentiation of CNS Stem Cells from Human Fetal Brain

In addition to the mulitpotentiality and self-renewing properties of CNS stem cells, the capacity to differentiate into one cell type in response to an extracellular signal is the key defining property of rodent CNS stem cells as demonstrated above. The three extracellular factors, PDGF, CNTF, and T3, also directed the differentiation of the human CNS cell clones in an identical manner (Table V; FIG. 6A–D). Thus, in the presence of PDGF, MAP2-positive neuronal cells increased to 71% of a clone, significantly higher than the 46% in the untreated control culture. In contrast, in the presence of CNTF, MAP2-positive cells decreased and GFAP-positive astrocytes increased dramatically to 85% of the clones. T3 increased O4- or GalC-positive oligodendroglial cells as well as GFAP-positive astroglial cells, while MAP2-positive neurons decreased (Table V). These results demonstrate the similarities quantitatively between the human and the rodent CNS stem cells and the universal applicability of the present culture system for efficient expansion and differentiation of mammalian CNS stem cells.

9. Maturation, Synaptogenesis, and Diversity of Stem Cell-Derived Neurons In Vitro Multipotentiality of CNS stem cells and their directed differentiation by defined extracellular signals unequivocally establish that neurons derive from stem cells directly. Thus, the origin of neuronal diversity seen in mature brain starts from CNS stem cells. Can the CNS stem cells expanded in culture for long-term retain the ability to mature to form axonal-dendritic polarity, to interact with other cells and form synapses? In order to investigate the extent to which CNS stem cell-derived neuron can mature in vitro under serum-free condition, stem cells derived from embryonic rat hippocampus were allowed to differentiate for up to 21 days at high density.

Subsequently, neurons were stained with various antibodies recognizing either axon- or dendrite-specific proteins. Synapsin, synaptophysin, synaptobrevin, and syntaxin are proteins found in synaptic vesicles of mature neurons at axon terminals and are involved in exocytosis of neurotransmitters. All four proteins were highly co-localized in the stem cell-derived neurons, in punctate pattern, most likely delineating the axon terminals. The processes bearing the synaptic vesicle proteins were thin, highly elaborate, traveled long distance, and decorated perimeter of neighboring neurons (FIG. 7G). They contained axon-specific proteins such as tau and neurofilament and were devoid of dendrite specific proteins such as MAP2a and MAP2b (FIG. 7H and 7I).

These results indicate that, similar to neurons generated in vivo, the stem cell-derived neurons display proper axon-dendrite polarity and exhibit synaptic activity. Stem cell-derived neurons also expressed major neurotransmitter receptors, transporters, and processing enzymes important for neurotransmitter functions. These included members of glutamate receptors, GABA receptors, and dopamine receptors (FIG. 8.). Furthermore, the stem cells retain their capacity to generate subtypes of neurons having molecular differences among the subtypes.

SIGNIFICANCE OF CNS STEM CELL TECHNOLOGY

Behavior of the stem cells in vitro provides important insights on the CNS development. Efficient proliferation and controlled differentiation of the precursor cells permitted a quantitative analysis of their developmental capacity. They display properties expected of stem cells: rapid proliferation, multipotentiality, and self-regeneration. Moreover, the cells from adult brain were quantitatively equivalent to the embryonic cells, indicating that stem cells persist in the adult.

The multipotential cells could be efficiently isolated from many regions of the developing CNS, indicating that they are abundant throughout the neuroepithelium. This contrasts with the widely-held notion that stem cells are rare. Differentiation of the stem cells can be effectively directed by extracellular factors that are known to be present during CNS development[16-23]. This suggests that different extracellular factors can act on a single class of stem cells to generate different cell types. A similar instructive mechanism has also been observed in vitro with stem cells isolated from the peripheral nervous system[24].

Multiple cell types appear rapidly when the stem cells are differentiated in vitro. In contrast, neurons, astrocytes, and oligodendrocytes appear at distinct times in vivo. Clearly, additional mechanisms must regulate the fate choice in vivo. Temporal and spatial expression of extracellular factors and their receptors may be a part of the mechanism.

Another mechanism of fate choice regulation in vivo may involve intermediate stages of differentiation. Identification of the bipotential oligodendrocyte precursor cell, O-2A, from postnatal optic nerve directly demonstrated that restricted progenitors are produced during development[25,26]. The stem cells are distinct from the O-2A cells. Their origins, properties, and developmental capacities differ. Given that the stem cells differentiate into oligodendrocytes, the differentiation pathway may involve an obligatory intermediate stage, a committed progenitor state like the O-2A cell. The similar responses of both cells to T3 and CNTF[27,28] may reflect this common step.

There is also evidence from lineage analysis in vivo and in vitro for the presence of other lineage restrictions, including bipotential neuronal and oligodendrocyte precursors and committed neuronal progenitors[6,7,29,30]. These may also arise from differentiating stem cells. The clonal assay described here will permit the relative contributions of lineage commitment versus instructive and selective factors on these intermediate cells to be quantitatively defined.

In summary, the present application reveals that:

(1) most regions of the fetal brain and spinal cord can be made to multiply in culture under completely defined culture conditions to yield up to a 1,000,000-fold increase in cell number;

(2) the homogeneous stem cell culture can be triggered to differentiate under precisely controlled conditions where up to 50% of the cells differentiate into neurons while the remaining cells become astrocytes and oligodendrocytes;

(3) many different kinds of neurons are generated in culture;

(4) growth factors have been identified that effectively direct the stem cells to differentiate into a single cell type, i.e., neuron, astrocyte, or oligodendrocyte; and (5) equivalent stem cells have been isolated and expanded from adult subependymal layer by using a similar procedure.

These enumerated results provide the following advantages over the current state of the art. First, this CNS stem cell technology permits large scale culture of homogeneous stem cells in an undifferentiated state. The longer that the cells can be maintained in the stem cell state, the higher the yield of neurons that can be derived from the culture, thereby enabling more efficient gene transfer and large scale selection of those cells carrying the gene of interest.

Second, this culture system permits controlled differentiation of the stem cells where 50% of the expanded cells now turn into neurons. This efficient differentiation, combined with efficient proliferation, routinely yields more than 100 million neurons from the neocortex of one fetal brain in a two-week period.

Third, the differentiation of the stem cells into neurons, astrocytes, and oligodendrocytes occurs constitutively where all three cell types continue to mature in culture, most likely due to nurturing interactions with each other, as during normal brain development. Many different types of neurons arise, which respond to many growth factors and contain neurotransmitters and their receptors. Thus, a significant portion of the brain development can be recapitulated in a manipulable environment, thereby highlighting the potential to extract and test novel neurotropic factors normally secreted by these cells.

Finally, these results permit the establishment of conditions by which dividing immature neurons can be derived directly from the stem cells and expanded further to allow large scale isolation of specific kinds of neurons in culture.

POTENTIAL COMMERCIAL APPLICATIONS

The stem cell technology of the present invention can be developed for direct application to many different aspects of therapy and drug discovery for nervous system disorders. Outlined below are four areas for potential commercial applications, i.e., gene therapy for Parkinson's disease, cell therapy, search for novel growth factors, and assays for drug screening.

The CNS stem cells more than meet the technical criteria as vehicles for gene therapies and cell therapies in general. The stem cells can be expanded rapidly under precisely controlled, reproducible conditions. Furthermore, these cells are readily accessible to all standard gene transfer protocols such as via retroviruses, adenoviruses, liposomes, and calcium phosphate treatment, as well as subsequent selection and expansion protocols. The expanded stem cells efficiently differentiate into neurons en masse.

In addition, it should be emphasized that two additional properties of the stem cells make them unique as the fundamental basis of biotechnology directed at the human nervous system. First, once stem cells are triggered to differentiate into mature cell types, all of the molecular interactions are in place within the culture system to generate, to mature, and to survive a variety of different cell types and neuronal subtypes. These interactions recapitulate a significant portion of the natural brain development process. Therefore, the stem cells, as vehicles of gene therapy and cell therapy, refurnish not only a single potential gene or factor to be delivered but also the whole infrastructure for nerve regeneration.

Second, the stem cells in culture are expanded from the multipotential germinal precursors of the normal brain development. Hence, these stem cells retain the capacity to become not only three different cell types but also many different types of neurons depending upon the environmental cues to which they are exposed. This broad plasticity, which is the inherent property of the stem cells, distinctly suggests that, once transplanted, the cells may retain the capacity to conform to many different host brain regions and to differentiate into neurons specific for that particular host region. These intrinsic properties of the primary stem cells are far different from the existing tumorigenic cell lines where some neuronal differentiation can be induced under artificial conditions. Therefore, with these unique properties, the expandable human CNS stem cells contain significant commercial potential by themselves with little further development.

1. Gene Therapy for Parkinson's Disease

Parkinson's Disease results mainly from degeneration of dopamine releasing neurons in the substantia nigra of the brain and the resulting depletion of dopamine neurotransmitter in the striatum. The cause of this degeneration is unknown but the motor degeneration symptoms of the disease can be alleviated by peripherally administering the dopamine precursor, L-dopa, at the early onset of the disease. As the disease continues to worsen, L-dopa is no longer effective and currently no further treatment is available. One promising treatment being developed is to transplant dopamine-rich substantia nigra neurons from fetal brain into the striatum of the brain of the patient. Results obtained from various clinical centers look extremely optimistic. However, it is estimated that up to 10 fetal brains are needed in order to obtain enough cells for one transplant operation. This requirement renders unfeasible the wide application of the transplantation of primary neurons as a therapeutic reality. This is exactly the type of problem solved by the CNS stem cell technology of the present application, whereby a small number of cells can be expanded in culture up to a 1,000,000 fold.

It is now widely recognized that transplantation of dopamine producing cells is the most promising therapy of severe Parkinson's Disease and that a stable cell population or cell line genetically engineered to produce dopamine is essential to effective therapy. Tyrosine hydroxylase (TH) is the key enzyme for dopamine synthesis. Human CNS stem cells derived from fetal basal ganglia can be produced which express the tyrosine hydroxylase (TH) gene. These cells can be expanded, differentiated, and transplanted into the patient's striatum. Since the cells are originally derived from the primordial striatum, they would have the best chance of integrating into this region of the brain. Production of such cells and their successful transplantation into animal models will result in the most promising application of gene therapy to date.

2. Cell Therapy

In most neurological diseases, unlike Parkinson's Disease, the underlying cause of symptoms cannot be attributed to a single factor. This condition renders the therapeutic approach of introducing a single gene by gene therapy ineffective. Rather, replacement of the host neuronal complex by healthy cells will be required. Since CNS stem cells are the natural germinal cells of the developing brain with the capacity to become the cells of the mature brain, the stem cells from the spinal cord and different regions of the brain may be used directly to repopulate degenerated nerves in various neuropathies.

Several specific stem cell lines that over express various growth factors that are currently in clinical trials are being developed. This application combines the unique plasticity of the stem cells and growth factor-mediated gene therapy to provide not only the benefit of the targeted delivery of the protein but also more broad neuronal regeneration in specific areas.

Primary examples of growth factors currently in clinical trials or under full development by various companies are listed below in Table VI[31]. So far, tests of growth factors have been limited to direct peripheral injection of large doses, which brings significant risks of side effects since most growth factors affect many different populations of neurons and non-neural tissues and with a short half-life. These problems can be overcome by generating from the CNS stem cells several cell populations or cell lines stably expressing these growth factors and demonstrating their capacity to differentiate into neurons and to secrete the growth factors in specific peripheral and central regions.

3. Search for Novel Growth Factors

One of the central principles of modern neurobiology is that each of the major projection neurons, if not all neurons, requires specific signals (trophic factors) to reach their target cells and survive. Neuropathies in many diseases may be caused by or involve lack of such growth factors. These growth factors represent the next generation of preventive and therapeutic drugs for nervous system disorders, and hence the enormous capitalization invested in the search and development of novel growth factors by the biotechnology industry.

Implicit in the observation that a variety of mature neurons can be produced from CNS stem cell culture is that various growth factors are secreted by the differentiating cells for determination of cell types, maturation, and continued support for their survival and that the cells contain the necessary receptor machinery to respond to those growth factors and probably others. Most of the growth factors known so far in the nervous system were discovered by their effects on peripheral nerves and they most likely represent a very minor fraction of existing growth factors in the brain.

Search for growth factors from the brain has been difficult mainly because particular neuronal cell types are difficult to isolate from the brain and maintain in defined culture conditions. Differentiation of the stem cells into neurons overcomes this problem and opens new assays to screen potential growth factors. The development of specific assays to search for novel growth factors in the embryonic CNS stem cells and purification and cloning of the new growth factors are already underway.

4. Assays for Drug Screening

As more and more neurotransmitter receptors and signal transducing proteins are being identified from the brain, it is becoming clear that the dogma of one neurotransmitter activating one receptor is an over-simplification. Most receptor complexes in neurons are composed of protein subunits encoded by several genes and each gene synthesizes many different variations of the protein. These variations result in a wide range of possible receptor combinations, and not a single receptor, that can interact with a neurotransmitter. Consequently, a range of signal output may be produced by a single neurotransmitter action. The specific signal effected by a neurotransmitter on a neuron, then, depends on which receptor complex is produced by the cell. Thus, cellular diversity must parallel the molecular diversity and constitute a major structural element underlying the complexity of brain function.

Drug discovery by traditional pharmacology had been performed without the knowledge of such complexity using whole brain homogenate and animals, and mostly produced analogs of neurotransmitters with broad actions and side effects. The next generation of pharmaceutical drugs aimed to modify specific brain functions may be obtained by screening potential chemicals against neurons displaying a specific profile of neurotransmitters, receptors complexes, and ion channels.

CNS stem cells expanded and differentiated into neurons in culture express several neurotransmitters and receptor complexes. Many cell lines derived from stem cells and neuronal progenitors of different regions of the brain can be developed which, when differentiated into mature neurons, would display a unique profile of neurotransmitter receptor complexes. Such neuronal cell lines will be valuable tools for designing and screening potential drugs.

In summary, the CNS stem cell technology of this application offers broad and significant potentials for treating nervous system disorders.

The following scientific articles have been cited throughout this application.

1. Turner, D. L. & Cepko, C. L., *Nature* 328, 131–136 (1987).
2. Gray, G., Glover, J., Majors, J. & Sanes, J., *Proc. Natl. Acad. Sci. USA* 85, 7356–7360 (1988).
3. Wetts, R. & Fraser, S., *Science* 239, 1142–1145 (1988).
4. McConnell, S., *Curr. Opin. Neurobiol.* 2, 23–27 (1992).
5. Walsh, C. & Cepko, C. L., *Nature* 362, 632–635 (1993).
6. Davis, A. A. & Temple, S., *Nature* 372, 263–266 (1994).
7. Williams, B. & Price, J., *Neuron* 14, 1181–1188 (1995).
8. Cattaneo, E. & McKay, R. D. G., *Nature* 347, 762–765 (1990).
9. Reynolds, B., Tetzlaff, W. & Weiss, S., *J. Neurosci.* 12, 4565–4574 (1992).
10. Ray, J., Peterson, D., Schinstine, M. & Gage, F., *Proc. Natl. Acad. Sci. USA* 90, 3602–3606 (1993).
11. Ghosh, A. & Greenberg, M., *Neuron* 15, 89–103 (1995).
12. Vicario-Abejon, C., Johe, K., Hazel, T., Collazo, D. & McKay, R., *Neuron* 15, 105–114 (1995).
13. Frederiksen, K. & McKay, R. D. G., *J. Neurosci.* 8, 1144–1151 (1988).
14. Lendahl, U., Zimmermann, L. B. & McKay, R. D. G., *Cell* 60, 585–595 (1990).
15. Reynolds, B. & Weiss, S., *Science* 255, 1707–1710 (1992).
16. Ip, N. et al., *Neuron* 10, 89–102 (1993).
17. Davis, S. et al., *Science* 260, 1805–1808 (1993).
18. Ware, C. et al., *Development* 121, 1283–1299 (1995).
19. Yeh, H. -J., Ruit, K. G., Wang, Y. -X., Parks, W. C., Snider, W. D. & Deuel, T. F., *Cell* 64, 209–216 (1991).
20. Yeh, H. -J., Silos-Santiago, I., Wang, Y. -X., George, R. J., Snider, W. D. & Deuel, T. F., *Proc. Natl. Acad. Sci., U.S.A.* 90, 1952–1956 (1993).
21. Orr-Urtregger, A., Bedford, M. T., Do, M. S., Eisenbach, L. & Lonai, P., *Development* 115, 289–303 (1992).
22. Reddy, U. R. & Pleasure, D., *J. Neurosci. Res.* 31, 670–677 (1992).
23. Barres, B. & Raff, M., *Neuron* 12, 935–942 (1994).
24. Shah, N. M., Marchionni, M. A., Isaacs, I., Stroobant, P. & Anderson, D. J., *Cell* 77, 349–360 (1994).
25. Raff, M., Miller, R. & Noble, M., *Nature* 303, 390–396 (1983).
26. Raff, M., *Science* 243, 1450–1455 (1989).
27. Barres, B., Lazar, M. & Raff, M., *Development* 120, 1097–1108 (1994).
28. Hughes, S., Lillien, L., Raff, M., Rohrer, H. & Sendtner, M., *Nature* 335, 70–73 (1988).
29. Luskin, M., Parnavelas, J. & Barfield, J., *J. Neurosci.* 13, 1730–1750 (1993).
30. Luskin, M., *FASEB J.* 8, 722–730 (1994).
31. Schatzle, H. M., *Trends in Neuroscience* 18, 463–464 (1995).
32. Sabate, O., Horellou, P., Vigne, E., Colin, P., Perricaudet, M., Buc-Caron, M. -H. & Mallet, J., *Nature Genetics* 9, 256–260 (1995).
33. Svendsen, C. N. & Rosser, A. E., *Trends in Neuroscience* 18, 465–466 (1995).
34. Gage, F. H., Ray, J. & Fisher, L. J., *Annu. Rev. Neurosci.* 18, 159–192 (1995).
35. Gage, F. H., Coates, P. W., Palmer, T. D., Kuhn, H. G., Fisher, L. J., Suhonen, J. O., Peterson, D. A., Suhr, S. T. & Ray, J., *Proc. Natl. Acad. Sci. USA* 92, 11879–11883 (1995).
36. Svendsen, C. N., Fawcett, J. W., Bentlage, C. & Dunnett, S. B., *Exp. Brain Res.* 102, 407–414 (1995).
37. Hermanson, M., Olsson, T., Westermark, B. & Funa K., *Exp. Brain Res.* 102, 415–422 (1995).
38. Kilpatrick, T. J., Richards, L. J., and Bartlett, P. F., *Mol. Cell. Neurosci.* 6, 2–15 (1995).
39. Ray, J. and Gage, F. H., *J. Neurosci.* 14, 3548–3564 (1994).
40. Gritti, A. et al., *J. Neurosci.* 16, 1091–1100 (1996).
41. Vescovi, A. L., Reynolds, B. A., Fraser, D. D., and Weiss, S., *Neuron* 11, 951–966 (1993).
42. Ahmed, S., Reynolds, B. A., and Weiss, S., *J. Neurosci.* 15, 5765–5778 (1995).10.11.
43. Kilpatrick, T. J. and Bartlett, P. F., *Neuron* 10, 255–265 (1993).

44. Kilpatrick, T. J. and Bartlett, P. F., *J. Neurosci.* 15, 3653–3661 (1995).

45. Baetge, E. E., *Ann. N.Y. Acad. Sci.* 695, 285 (1993).

46. Bartlett, P. F. et al., *Clin. Exp. Pharm. Physiol.* 22, 559–562 (1995).

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and scientific articles cited herein are hereby incorporated by reference in their entirety and relied upon.

TABLE I

CELL TYPE COMPOSITION OF DIFFERENTIATED CLONES
Clones of Embryonic Hippocampal Precursor Cells

| Passage | Clone Size | MAP2+ (%) | GalC+ (%) | GFAP+ (%) |
|---|---|---|---|---|
| 1 | 319 | 145 (45) | | 41 (13) |
| 1 | 451 | 245 (54) | | 0 (0) |
| 1 | 1237 | 634 (51) | | 9 (1) |
| 1 | 2197 | 956 (44) | | 42 (2) |
| 1 | 2779 | 1617 (58) | | 336 (12) |
| 4 | 71 | | 10 (14) | 5 (7) |
| 4 | 139 | | 14 (10) | 4 (3) |
| 4 | 296 | | 21 (7) | 139 (47) |
| 4 | 341 | | 54 (16) | 38 (11) |
| 4 | 420 | | 39 (9) | 25 (6) |
| 4 | 600 | | 35 (6) | 60 (10) |
| 4 | 662 | | 66 (10) | 62 (9) |
| 4 | 141 | 42 (30) | 4 (3) | |
| 4 | 427 | 220 (52) | 15 (4) | |
| 4 | 610 | 306 (50) | 29 (5) | |
| Total Average: | | 48.6 ± 1.6% | 8.4 ± 1.0% | 7.8 ± 2.3% |

TABLE II

CELL TYPE COMPOSITION OF DIFFERENTIATED CLONES
Subclones from Clones of Embryonic Hippocampal Precursor Cells

| Subclone | Clone Size | MAP2+ (%) | GalC+ (%) | GFAP+ (%) |
|---|---|---|---|---|
| HI6.1 | 337 | 22 (7) | | 99 (29) |
| HI6.2 | 338 | 13 (4) | | 157 (46) |
| HI6.3 | 537 | 132 (25) | | 48 (9) |
| HI6.4 | 565 | 98 (17) | | 28 (5) |
| HI6.5 | 831 | 96 (12) | | 107 (13) |
| HI6.6 | 886 | 158 (18) | | 134 (15) |
| HI6.7 | 893 | 135 (15) | | 66 (7) |
| HI6.8 | 950 | 154 (16) | | 53 (6) |
| HI6.9 | 951 | 112 (12) | | 120 (13) |
| HI6.10 | 970 | 105 (11) | | 95 (10) |
| HI19.1 | 84 | 11 (13) | | 0 (0) |
| HI19.2 | 211 | 45 (21) | | 0 (0) |
| HI19.3 | 363 | 61 (17) | | 18 (5) |
| HI19.4 | 697 | 172 (25) | | 5 (1) |
| HI19.5 | 861 | 135 (16) | | 57 (7) |
| HI19.6 | 1469 | 401 (27) | | 123 (8) |
| HI19.7 | 1841 | 486 (26) | | 179 (10) |
| HI8.1 | 88 | | 4 (5) | 0 (0) |
| HI8.2 | 104 | | 3 (3) | 0 (0) |
| HI8.3 | 193 | | 16 (8) | 28 (15) |
| HI8.4 | 237 | | 14 (6) | 39 (16) |
| HI8.5 | 384 | | 65 (17) | 119 (31) |
| HI8.6 | 402 | | 26 (6) | 75 (19) |
| HI8.7 | 554 | | 49 (9) | 45 (8) |
| HI8.8 | 571 | | 23 (4) | 49 (9) |
| HI8.9 | 662 | | 41 (6) | 118 (18) |
| HI8.10 | 669 | | 46 (7) | 46 (7) |
| HI8.11 | 827 | | 57 (7) | 18 (2) |
| HI8.12 | 836 | | 92 (11) | 97 (12) |
| HI8.13 | 1084 | | 104 (10) | 53 (5) |
| HI8.14 | 1268 | | 124 (10) | 163 (13) |
| HI8.15 | 1284 | | 75 (6) | 193 (15) |
| Total Average: | | 20.1 ± 1.4% | 8.9 ± 1.1% | 10.0 ± 0.7% |

TABLE III

CELL TYPE COMPOSITION OF DIFFERENTIATED CLONES
Clones of Adult Subependymal Cells

| Passage | Clone Size | MAP2+ (%) | GalC+ (%) | GFAP+ (%) |
|---|---|---|---|---|
| 1 | 73 | 6 (8) | | 37 (51) |
| 1 | 159 | 56 (35) | | 42 (26) |
| 1 | 173 | 57 (33) | | 26 (15) |
| 1 | 185 | 71 (38) | | 32 (17) |
| 1 | 230 | 97 (42) | | 39 (17) |
| 1 | 273 | 139 (51) | | 56 (21) |
| 1 | 387 | 117 (30) | | 45 (12) |
| 1 | 554 | 237 (43) | | 84 (15) |
| 1 | 675 | 280 (41) | | 74 (11) |
| 1 | 847 | 399 (47) | | 155 (18) |
| 1 | 496 | | 23 (5) | 92 (19) |
| 1 | 526 | | 7 (1) | 115 (22) |
| 1 | 644 | | 19 (3) | 26 (4) |
| 1 | 713 | | 22 (3) | 179 (25) |
| 1 | 1112 | | 56 (5) | 235 (21) |
| 0 | 278 | 153 (55) | | 6 (2) |
| 0 | 305 | 145 (48) | | 19 (6) |
| 1 | 411 | 156 (38) | | 68 (17) |
| 0 | 513 | 242 (47) | | 3 (1) |
| 0 | 532 | 246 (46) | | 26 (5) |
| 0 | 538 | 283 (53) | | 10 (2) |
| 0 | 584 | 277 (47) | | 32 (5) |
| 0 | 1012 | 498 (49) | | 5 (0) |
| Total Average: | | 41.7 ± 2.6% | 4.2 ± 1.2% | 19.6 ± 2.7% |

TABLE IV

EFFECT OF EXTRACELLULAR FACTORS
ON CELL TYPE DETERMINATION

| | (Antibody) | Untreated (%) | +PDGF (%) | +CNTF (%) | +T3 (%) |
|---|---|---|---|---|---|
| A. Embryonic | | | | | |
| Neuron | (MAP2) | 45.9 | 81.0 | 0.9 | 11.5 |
| Neuron | (TuJ1) | 9.9 | 72.4 | N.D. | N.D. |
| Neuron | (NF-M) | 1.0 | 53.0 | N.D. | N.D. |
| Oligodendrocyte | (GalC) | 7.4 | 2.8 | 4.5 | 21.2 |
| Astrocyte | (GFAP) | 6.3 | 2.0 | 97.3 | 20.7 |
| B. Adult | | | | | |
| Neuron | (MAP2) | 36.8 | 73.9 | 11.8 | 35.2 |
| Neuron | (TuJ1) | 47.9 | 72.4 | N.D. | N.D. |
| Oligodendrocyte | (GalC) | 4.8 | N.D. | N.D. | 47.4 |
| Astrocyte | (GFAP) | 20.3 | 2.2 | 72.9 | 32.4 |

TABLE V

DIRECTED DIFFERENTIATION OF bFGF-EXPANDED HUMAN CNS STEM CELLS

| (Antibody) | Untreated (%) | +PDGF (%) | +CNTF (%) | +T3 (%) |
|---|---|---|---|---|
| Neuron (MAP2+) | 45.9 ± 2.3 | 71.4 ± 1.9 | 9.4 ± 1.6 | 16.9 ± 2.4 |
| Oligodendrocytes (O4+/Galc+) | 2.6 ± 0.8 | 0.8 ± 0.3 | 0.9 ± 0.1 | 25.3 ± 2.8 |
| Astrocytes (GFAP+) | 10.5 ± 1.8 | 7.1 ± 1.2 | 85.2 ± 1.9 | 37.1 ± 3.4 |
| Dead | 5.9 ± 0.7 | 3.5 ± 0.4 | 2.0 ± 0.5 | 8.2 ± 0.6 |

TABLE VI

NEUROTROPIC FACTORS AND DISEASES

| Neurotropic factor | Disease |
|---|---|
| Nerve growth factor | Alzheimer's Disease |
| | Diabetic neuropathy |
| | Taxol neuropathy |
| | Compressive neuropathy |
| | AIDS-related neuropathy |
| Brain-derived growth factor | Amyotrophic lateral sclerosis |
| Neurotrophin 3 | Large fiber neuropathy |
| Insulin-like growth factor | Amyotrophic lateral sclerosis |
| | Vincristine neuropathy |
| | Taxol neuropathy |
| Ciliary neurotrophic factor | Amyotrophic lateral sclerosis |
| Glia-derived neurotrophic factor | Parkinson's Disease |

What is claimed is:

1. A method for expansion and culture in vitro of stem cells of the central nervous system of a mammal, wherein the stem cells maintain the multipotential capacity to differentiate into neurons, astrocytes, and oligodendrocytes, comprising the steps of:

a) dissociating cells from central nervous system tissue by mechanical trituration in the absence of divalent cations;

b) culturing the dissociated cells adhered onto a plate in a chemically defined serum-free culture medium;

c) plating dissociated cells at a density not exceeding 20,000 cells/cm$^2$ and, in subsequent passages, replating the cultured cells at a density not exceeding 10,000 cells/cm$^2$;

d) adding daily to the cultured cells a growth factor selected from the group consisting of
   i) bFGF at a concentration of at least 10 ng/ml,
   ii) EGF at a concentration of at least 10 ng/ml,
   iii) TGF-alpha at a concentration of at least 10 ng/ml, and
   iv) aFGF at a concentration of at least 10 ng/ml plus 1 µg/ml heparin;

e) replacing the culture medium with fresh medium within every two days;

f) passaging the cultured cells within four days after plating so as not to exceed 50% confluence; and g) passaging the cultured cells by treating the cultured cells with saline solution free of divalent cations and scraping cells from the plate.

2. The method of claim 1, wherein the stem cells are derived from central nervous system tissue from a human.

3. The method of claim 2, wherein the stem cells are derived from central nervous system tissue from a fetus.

4. The method of claim 3, wherein the stem cells are derived from central nervous system tissue selected from the group consisting of hippocampus, cerebral cortex, striatum, septum, diencephalon, mesencephalon, hindbrain, and spinal cord.

5. The method of claim 2, wherein the stem cells are derived from central nervous system tissue from an adult.

6. An in vitro adhesion culture of stem cells of the central nervous system of a mammal, wherein the stem cells a) maintain the multipotential capacity to differentiate into neurons, astrocytes, and oligodendrocytes;

b) divide in serum-free medium supplemented with a mitogen; and c) differentiate upon withdrawal of mitogen.

7. The in vitro culture of claim 6, wherein the stem cells are derived from central nervous system tissue from a human.

8. The in vitro culture of claim 7, wherein the stem cells are derived from central nervous system tissue from a fetus.

9. The in vitro culture of claim 8, wherein the stem cells are derived from central nervous system tissue selected from the group consisting of hippocampus, cerebral cortex, striatum, septum, diencephalon, mesencephalon, hindbrain, and spinal cord.

10. The in vitro culture of claim 7, wherein the stem cells are derived from central nervous system tissue from an adult.

11. The in vitro culture of claim 10, wherein the stem cells are derived from central nervous system tissue selected from the group consisting of hippocampus, cerebral cortex, striatum, septum, diencephalon, mesencephalon, hindbrain, and spinal cord.

12. The in vitro culture of claim 6, wherein the stem cells differentiate to mature neurons exhibiting:

a) axon-dendrite polarity, b) synaptic terminals, and c) localization of proteins involved in synaptogenesis and synaptic activity including
   i) neurotransmitter receptors,
   ii) transporters, and
   iii) processing enzymes.

13. The in vitro culture of claim 6, wherein the stem cells retain their capacity to generate subtypes of neurons having molecular differences among the subtypes.

14. A method for differentiation of an in vitro culture of stem cells of the central nervous system of a mammal, wherein the stem cells maintain the multipotential capacity to differentiate into neurons, astrocytes, and oligodendrocytes, comprising the steps of:

a) dissociating cells from central nervous system tissue by mechanical trituration in the absence of divalent cations;

b) culturing the dissociated cells adhered onto a plate in a chemically defined serum-free culture medium;

c) plating dissociated cells at a density not exceeding 20,000 cells/cm$^2$ and, in subsequent passages, replating the cultured cells at a density not exceeding 10,000 cells/cm$^2$;

d) adding daily to the cultured cells a first growth factor selected from the group consisting of
   i) bFGF at a concentration of at least 10 ng/ml, ii) EGF at a concentration of at least 10 ng/ml, iii) TGF-alpha at a concentration of at least 10 ng/ml, and iv) aFGF at a concentration of at least 10 ng/ml plus 1 µg/ml heparin;

e) replacing the culture medium with fresh medium within every two days;

f) passaging the cultured cells within four days after plating so as not to exceed 50% confluence:

g) passaging the cultured cells by treating the cultured cells with saline solution free of divalent cations and scraping cells from the plate; and h) removing the first growth factor from the cultured cells, wherein said removal results in differentiation of the cultured cells into neurons, astrocytes, and/or oligodendrocytes.

15. The method of claim 14, further comprising adding a second growth factor to the cultured cells after removing the first growth factor from the cultured cells.

16. The method of claim 15, wherein the second growth factor is selected from the group consisting of platelet-derived growth factor (PDGF), ciliary neurotropic factor (CNTF), leukemia inhibitory factor (LIF), and thyroid hormone, iodothyronine (T3).

* * * * *

US005753506C1

(12) EX PARTE REEXAMINATION CERTIFICATE (5382nd)
United States Patent
Johe

(10) Number: US 5,753,506 C1
(45) Certificate Issued: May 30, 2006

(54) ISOLATION PROPAGATION AND DIRECTED DIFFERENTIATION OF STEM CELLS FROM EMBRYONIC AND ADULT CENTRAL NERVOUS SYSTEM OF MAMMALS

(75) Inventor: Karl K. Johe, Potomac, MD (US)

(73) Assignee: Neuralstem, Inc., Gaithersburg, MD (US)

Reexamination Request:
No. 90/006,807, Oct. 8, 2003

Reexamination Certificate for:
Patent No.: 5,753,506
Issued: May 19, 1998
Appl. No.: 08/719,450
Filed: Sep. 25, 1996

Related U.S. Application Data
(60) Provisional application No. 60/018,206, filed on May 23, 1996.

(51) Int. Cl.
*C12N 5/08* (2006.01)

(52) U.S. Cl. .................. 435/377; 435/325; 435/366; 435/368
(58) Field of Classification Search ................ 435/325, 435/352, 363, 366, 368, 375, 377
See application file for complete search history.

(56) References Cited

U.S. PATENT DOCUMENTS

| | | | | |
|---|---|---|---|---|
| 5,340,740 A | * | 8/1994 | Petitte et al. | 435/349 |
| 5,486,359 A | * | 1/1996 | Caplan et al. | 424/93.7 |
| 5,654,183 A | | 8/1997 | Anderson | |
| 5,750,376 A | | 5/1998 | Weiss et al. | |

OTHER PUBLICATIONS

American Heritage Dictionary of the English Language (downloaded from Dictionary.com Jan. 21, 2005).*
Takeichi & Okada (1972) "Roles of Magnesium and Calcium Ions in Cell–to–Substrate Adhesion." Experimental Cell Research 74(1): 51–60.*
Sigma Aldrich MSDS and Information on EDTA and EGTA (downloaded from website on Jan. 21, 2005).*
Nolte The Human Brain: An Introduction to Its Functional Anatomy (4th Edition) Chapter 1: Introduction to the Nervous System (pp. 1–35).*
Von Visger et al. (Jul. 1994) "Differentiation and maturation of astrocytes derived from neuroepithelial progenitor cells in culture." Exp Neurol. 128(1): 34–40.*
Invitrogen website Aug. 31, 2004: HBSS Media Formulation.*

* cited by examiner

*Primary Examiner*—Brenda Brumback

(57) ABSTRACT

The present invention reveals an in vitro procedure by which a homogeneous population of multipotential precursor cells from mammalian embryonic neuroepithelium (CNS stem cells) can be expanded up to $10^9$ fold in culture while maintaining their multipotential capacity to differentiate into neurons, oligodendrocytes, and astrocytes. Chemically defined conditions are presented that enable a large number of neurons, up to 50% of the expanded cells, to be derived from the stem cells. In addition, four factors—PDGF, CNTF, LIF, and T3—have been identified which, individually, generate significantly higher proportions of neurons, astrocytes, or oligodendrocytes. These defined procedures permit a large-scale preparation of the mammalian CNS stem cells, neurons, astrocytes, and oligodendrocytes under chemically defined conditions with efficiency and control. These cells should be an important tool for many cell- and gene-based therapies for neurological disorders.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 6 and 14 are determined to be patentable as amended.

Claims 2–5, 7–13 and 15–16, dependent on an amended claim, are determined to be patentable.

New claim 17 is added and determined to be patentable.

1. A method for expansion [and] *of an adhesion* culture in vitro of stem cells of the central nervous system of a mammal, wherein the stem cells maintain the multipotential capacity to differentiate into neurons, astrocytes, and oligodendrocytes, *and propagate without aggregating into spheres until at least about 50% confluence* comprising the steps of:
   a) dissociating cells from central nervous system tissue by mechanical trituration in the absence of divalent cations;
   b) culturing the dissociated cells adhered onto a plate in a chemically defined serum-free culture medium;
   c) plating dissociated cells at a density not exceeding 20,000 cells/cm² and, in subsequent passages, replating the cultured cells at a density not exceeding 10,000 cells/cm²;
   d) adding daily to the cultured cells a growth factor selected from the group consisting of
      i) bFGF at a concentration of at least 10 ng/ml,
      ii) EGF at a concentration of at least 10 ng/ml,
      iii) TGF-alpha at a concentration of at least 10 ng/ml, and
      iv) aFGF at a concentration of at least 10 ng/ml plus 1 µg/ml heparin;
   e) replacing the culture medium with fresh medium within every two days;
   f) passaging the cultured cells within four days after plating so as not to exceed 50% confluence; and
   g) passaging the cultured cells by treating the cultured cells with saline solution free of divalent cations and scraping cells from the plate.

6. An in vitro adhesion culture of stem cells of the central nervous system of a mammal, wherein the stem cells
   a) maintain the multipotential capacity to differentiate into neurons, astrocytes, and oligodendrocytes;
   b) divide in serum-free medium supplemented with a mitogen *without aggregating into spheres until at least about 50% confluence*; and
   c) differentiate upon withdrawal of mitogen.

14. A method for differentiation of an in vitro *adhesion* culture of stem cells of the central nervous system of a mammal, wherein the stem cells maintain the multipotential capacity to differentiate into neurons, astrocytes, and oligodendrocytes, *and propagate without aggregating into spheres until at least about 50% confluence* comprising the steps of:
   a) dissociating cells from central nervous system tissue by mechanical trituration in the absence of divalent cations;
   b) culturing the dissociated cells adhered onto a plate in a chemically defined serum-free culture medium;
   c) plating dissociated cells at a density not exceeding 20,000 cells/cm² and, in subsequent passages, replating the cultured cells at a density not exceeding 10,000 cells/cm²;
   d) adding daily to the cultured cells a first growth factor selected from the group consisting of
      i) bFGF at a concentration of at least 10 ng/ml,
      ii) EGF at a concentration of at least 10 ng/ml,
      iii) TGF-alpha at a concentration of at least 10 ng/ml, and
      iv) aFGF at a concentration of at least 10 ng/ml plus 1 µg/ml heparin;
   e) replacing the culture medium with fresh medium within every two days;
   f) passaging the cultured cells within four days after plating so as not to exceed 50% confluence;
   g) passaging the cultured cells by treating the cultured cells with saline solution free of divalent cations and scraping cells from the plate; and
   h) removing the first growth factor from the cultured cells, wherein said removal results in differentiation of the cultured cells into neurons, astrocytes, and/or oligodendrocytes.

*17. The in vitro culture of claim 6, wherein the culture includes stem cells that divide into daughter cells wherein each daughter cell is a stem cell.*

* * * * *

(12) EX PARTE REEXAMINATION CERTIFICATE (7850th)
United States Patent
Johe

(10) Number: US 5,753,506 C2
(45) Certificate Issued: Nov. 2, 2010

(54) ISOLATION PROPAGATION AND DIRECTED DIFFERENTIATION OF STEM CELLS FROM EMBRYONIC AND ADULT CENTRAL NERVOUS SYSTEM OF MAMMALS

(75) Inventor: Karl K. Johe, Potomac, MD (US)

(73) Assignee: Neuralstem, Inc., Gaithersburg, MD (US)

Reexamination Request:
No. 90/009,567, Sep. 2, 2009

Reexamination Certificate for:
Patent No.: 5,753,506
Issued: May 19, 1998
Appl. No.: 08/719,450
Filed: Sep. 25, 1996

Reexamination Certificate C1 5,753,506 issued May 30, 2006

Related U.S. Application Data
(60) Provisional application No. 60/018,206, filed on May 23, 1996.

(51) Int. Cl.
*C12N 5/08* (2006.01)

(52) U.S. Cl. .................. 435/377; 435/325; 435/663; 435/368

(58) Field of Classification Search .................. None
See application file for complete search history.

(56) References Cited

U.S. PATENT DOCUMENTS 6,399,369 B1    6/2002    Weiss et al. .............. 435/320.1

FOREIGN PATENT DOCUMENTS

WO    WO 93/01275    1/1993

OTHER PUBLICATIONS

Baas, et al., "Polarity orientation of microtubules in hippocampal neurons: Uniformity in the axon and nonuniformity in the dendrite". Proc. Natl. Acad. Sci. USA, vol. 85, pp. 8335–8339, Nov. 1988.*
Davis and Temple, "A self-renewing multipotential stem cell in embryonic rat cerebral cortex", *Nature,* 372, pp. 263–268 (1994).
Reynolds et al., "EGF– and TGFα–responsive striatal embryonic progenitor cells produce both neurons and astrocytes", *Society of Neuroscience Abstracts,* 15, pp. 1147, Abstract No. 474.2 (1990).
Reynolds et al., "A multipotent EGF–responsive striatal embryonic progenitor cell produces neurons and astrocytes", *J. Neuroscience,* 12, pp. 4565–4574 (1992).
Takeichi and Okada, "Roles of magnesium and calcium ions in cell–to–substrate adhesion", *Experimental Cell Research* 74, pp. 51–60 (1972).

\* cited by examiner

*Primary Examiner*—Brenda Brumback

(57) ABSTRACT

The present invention reveals an in vitro procedure by which a homogeneous population of multipotential precursor cells from mammalian embryonic neuroepithelium (CNS stem cells) can be expanded up to $10^9$ fold in culture while maintaining their multipotential capacity to differentiate into neurons, oligodendrocytes, and astrocytes. Chemically defined conditions are presented that enable a large number of neurons, up to 50% of the expanded cells, to be derived from the stem cells. In addition, four factors—PDGF, CNTF, LIF, and T3—have been identified which, individually, generate significantly higher proportions of neurons, astrocytes, or oligodendrocytes. These defined procedures permit a large-scale preparation of the mammalian CNS stem cells, neurons, astrocytes, and oligodendrocytes under chemically defined conditions with efficiency and control. These cells should be an important tool for many cell- and gene-based therapies for neurological disorders.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-17 is confirmed.

1. A method for expansion [and] *of an adhesion* culture in vitro of stem cells of the central nervous system of a mammal, wherein the stem cells maintain the multipotential capacity to differentiate into neurons, astrocytes, and oligodendrocytes, *and propagate without aggregating into spheres until at least about 50% confluence* comprising the steps of:
   a) dissociating cells from central nervous system tissue by mechanical trituration in the absence of divalent cations;
   b) culturing the dissociated cells adhered onto a plate in a chemically defined serum-free culture medium;
   c) plating dissociated cells at a density not exceeding 20,000 cells/cm$^2$ and, in subsequent passages, replating the cultured cells at a density not exceeding 10,000 cells/cm$^2$;
   d) adding daily to the cultured cells a growth factor selected from the group consisting of
      i) bFGF at a concentration of at least 10 ng/ml,
      ii) EGF at a concentration of at least 10 ng/ml,
      iii) TGF-alpha at a concentration of at least 10 ng/ml, and
      iv) aFGF at a concentration of at least 10 ng/ml plus 1 µg/ml heparin;
   e) replacing the culture medium with fresh medium within every two days;
   f) passaging the cultured cells with four days after plating so as not to exceed 50% confluence; and
   g) passaging the cultured cells by treating the cultured cells with saline solution free of divalent cations and scraping cells from the plate.

* * * * *